US008244480B2

(12) United States Patent
Doi

(10) Patent No.: US 8,244,480 B2
(45) Date of Patent: Aug. 14, 2012

(54) COMPUTER PRODUCT, ANALYSIS SUPPORT APPARATUS, AND ANALYSIS SUPPORT METHOD

(75) Inventor: Kentarou Doi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/751,146

(22) Filed: Mar. 31, 2010

(65) Prior Publication Data

US 2010/0185400 A1    Jul. 22, 2010

Related U.S. Application Data

(63) Continuation of application No. PCT/JP2007/069314, filed on Oct. 2, 2007.

(51) Int. Cl.
| | |
|---|---|
| G06F 19/10 | (2011.01) |
| G06F 19/18 | (2011.01) |
| G06F 17/40 | (2006.01) |
| G06F 17/00 | (2006.01) |
| G06F 19/00 | (2011.01) |
| A61B 10/00 | (2006.01) |
| A61B 19/00 | (2006.01) |

(52) U.S. Cl. ............. 702/20; 340/540; 600/300; 702/19
(58) Field of Classification Search .................. 73/432.1, 73/865.8, 866; 340/500, 540; 435/4; 436/63, 436/811, 815; 600/300; 702/1, 19, 20, 127, 702/182, 187, 189; 707/600, 602, 687, 692, 707/705, 722, 758, 899
See application file for complete search history.

(56) References Cited

U.S. PATENT DOCUMENTS 5,837,464 A * 11/1998 Capon et al. ...................... 435/6

(Continued)

FOREIGN PATENT DOCUMENTS

JP    2003-203078    7/2003

(Continued)

OTHER PUBLICATIONS

Tanaka, T. et al., Pharmacogenomics of cardiovascular pharmacology: Pharmacogenomic Network of Cardiovascular Disease Models, Journal of Pharmacological Sciences, vol. 107, No. 1, pp. 8-14 2008 (Abstract Only).*
PubMed, URL:ncbi.nlm.nih.gov/entrez/query.fcgi (1 pg.).
KEGG Pathway Database, URL:genome.jp/kegg/pathway.html (7 pp.).

(Continued)

*Primary Examiner* — Edward Cosimano
(74) *Attorney, Agent, or Firm* — Staas & Halsey LLP

(57) ABSTRACT

A non-transitory computer-readable recording medium stores therein an analysis support program causing a computer to execute receiving test result data identifying an analysis subject molecule, and quantity-changing molecules that have changed in quantity due to administration or deficiency of the analysis subject molecule in a test subject; acquiring a first pathway indicating an interaction between the quantity-changing molecules identified by the test result data and a second pathway indicating a molecular interaction with the analysis subject molecule, from a database storing therein for each molecular interaction, a type; determining from among biological phenomena correlated with the interaction between quantity-changing molecules of the first pathway, determines a biological phenomenon other than a biological phenomenon correlated with a molecular interaction of the second pathway to be a novel biological phenomenon caused by administration or deficiency of the analysis subject molecule; and outputting a determination result obtained at the determining.

17 Claims, 19 Drawing Sheets

U.S. PATENT DOCUMENTS

| | | | |
|---|---|---|---|
| 6,242,187 B1 * | 6/2001 | Capon et al. | 435/6 |
| 6,387,637 B1 * | 5/2002 | Levin et al. | 435/7.1 |
| 6,942,969 B2 * | 9/2005 | Capon et al. | 435/6 |
| 7,279,279 B2 * | 10/2007 | Capon et al. | 435/6 |
| 7,354,708 B2 * | 4/2008 | Hall et al. | 435/6 |
| 2002/0182599 A1 * | 12/2002 | Fishman | 435/6 |
| 2002/0187486 A1 * | 12/2002 | Hall et al. | 435/6 |
| 2002/0197696 A1 * | 12/2002 | Levin et al. | 435/200 |
| 2003/0008282 A1 * | 1/2003 | Capon et al. | 435/6 |
| 2003/0158672 A1 * | 8/2003 | Ramnarayan et al. | 702/19 |
| 2004/0265841 A1 * | 12/2004 | Fishman et al. | 435/6 |
| 2005/0080773 A1 | 4/2005 | Koike et al. | |
| 2005/0214746 A1 * | 9/2005 | Capon et al. | 435/5 |
| 2006/0004706 A1 | 1/2006 | Tomioka et al. | |
| 2006/0106544 A1 | 5/2006 | Ohta et al. | |
| 2007/0005260 A1 | 1/2007 | Yokoyama et al. | |

FOREIGN PATENT DOCUMENTS

| | | |
|---|---|---|
| JP | 2005-122231 | 5/2005 |
| JP | 2006-146380 | 6/2006 |
| JP | 2007-11996 | 1/2007 |
| WO | 03/077159 | 9/2003 |
| WO | 2005/050518 | 6/2005 |

OTHER PUBLICATIONS

BioCarta, URL:biocarta.com/ (1 pg.).
MeSH, URL:nlm.nih.gov/mesh/meshhome.html (1 pg.).
OMIM, URL:ncbi.nlm.nih.gov/entrez/query. fcgi?db=0MIM (1 pg.).
H-inv DB, URL:jbic.or.jp/activity/i_db_pyh-inv_db.html (4 pp.).
BioCreAtIvE, URL:/biocreative.sourceforge.net/ (2 pp.).
Human Protein Reference Database, URL:.hprd.org/ (2 pp.).
International Search Report, mailed Dec. 25, 2007, in corresponding International Application No. PCT/JP2007/069314 (6 pp.).
Written Opinion of the International Searching Authority, mailed Dec. 25, 2007, in corresponding International Application No. PCT/JP2007/069314 (5 pp.).
International Preliminary Report on Patentability, mailed Apr. 15, 2010, in corresponding PCT Application No. PCT/JP2007/069314 (5 pp.).
English Translation of the International Preliminary Report on Patentability issued May 4, 2010 in corresponding International Patent Application PCT/JP2007/069314.

* cited by examiner

FIG.3

MEDICAL REFERENCES DB ~300

| REFERENCE ID | TITLE | ABSTRACT | AUTHOR | DATE OF PUBLICATION | MeSH TERM |
|---|---|---|---|---|---|
| 12235730 | Therapeutische Umschau. Revue therapeutique | The major risk factor for the development of insulin resistance and type 2 diabetes is obesity. A key role is ... | Stockli R, Keller U. | 2002 Aug | Adipose Tissue<br>Diabetes Mellitus<br>Diabetes Mellitus, Type 2<br>Energy Metabolism<br>Humans<br>Insulin Resistance<br>Obesity<br>Risk Factors |
| 15725700 | Nuclear receptors as targets for drug development: crosstalk between ... | Peroxisome proliferator-activated receptor gamma (PPARgamma) is a ligand-dependent nuclear receptor and regulates adipogenesis and fat metabolism. PPARgamma is activated by ... | Takada I, Suzawa M, Kato S. | 2005 Feb | Animals<br>Bone Marrow Cells<br>Cytokines<br>Drug Delivery Systems<br>Humans<br>Mesenchymal Stem Cells<br>PPAR gamma<br>Pharmaceutical Preparations<br>Receptor Cross-Talk |
| 15877288 | Peroxisome proliferator-activated receptor-gamma agonist rosiglitazone reduces clinical ... | Rosiglitazone, an agonist of peroxisome proliferator-activated receptor-gamma (PPAR gamma), is an insulin-sensitizing antidiabetic agent and inhibits restenosis in animal blood vessels. However ... | Wang G, Wei J, Guan Y, Jin N, Mao J, Wang X. | 2005 May | Aged<br>Angioplasty, Transluminal, Percutaneous Coronary<br>C-Reactive Protein<br>Chemokine CCL2<br>Chemokines<br>Coronary Disease<br>Diabetes Mellitus, Type 2<br>Diabetic Angiopathies |
| ... | ... | ... | ... | ... | ... |

QUANTITY-CHANGING PATTERN DB — 500

| PATTERN ID | QUANTITY-CHANGING MOLECULES | | |
|---|---|---|---|
| P1 | D | E | F |
|  | ↑ | ↑ | ↑ |
| P2 | D | E | F |
|  | ↓ | ↑ | ↓ |
| P3 | D | E | F |
|  | ↑ | ↓ | ↑ |
| ⋮ | ⋮ | ⋮ | ⋮ |

| TEST RESULT DATA | ANALYSIS SUBJECT MOLECULE: X | |
|---|---|---|
| QUANTITY-CHANGING MOLECULE | QUANTITY | |
| | BEFORE ADMINISTRATION | AFTER ADMINISTRATION |
| D | Qd | QD |
| E | Qe | QE |
| F | Qf | QF |

| TEST RESULT (CORRELATION WITH QUANTITY-CHANGING MOLECULE) | | CORRELATION WITH PHARMACEUTICAL X | | RATIO ($\alpha/\beta$) |
|---|---|---|---|---|
| BIOLOGICAL PHENOMENON | CORRELATION LEVEL $\alpha$ | BIOLOGICAL PHENOMENON | CORRELATION LEVEL $\beta$ | |
| DIABETES | 2 | DIABETES | 1 | 2 |
| ASTHMA | 1 | ASTHMA | 2 | 0.5 |
| RHEUMATISM | 1 | RHEUMATISM | 0 | ∞ |
| COLD | 0 | COLD | 1 | 0 |
| COLON CANCER | 0 | COLON CANCER | 3 | 0 |

T1 / T2

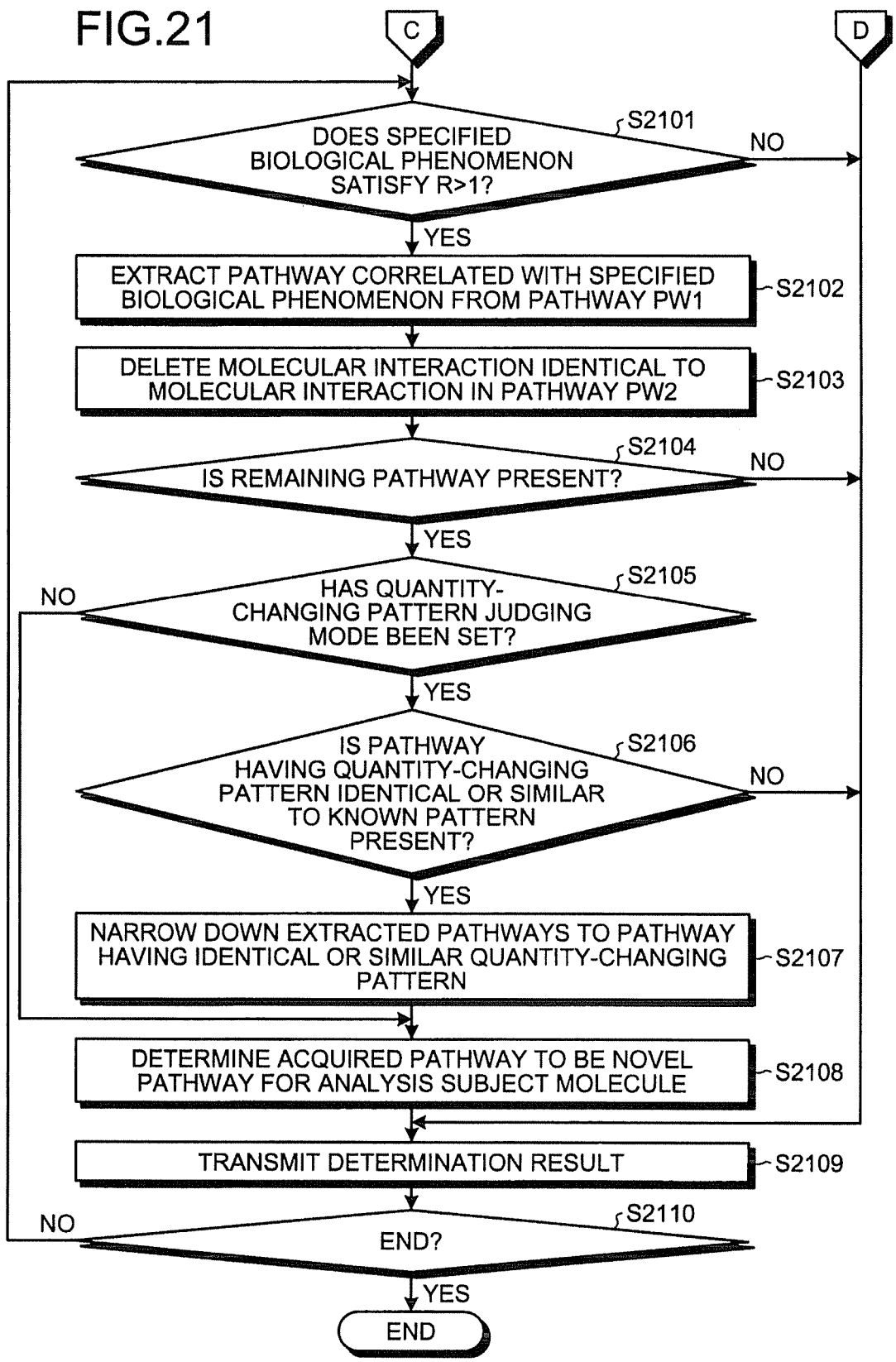

COMPUTER PRODUCT, ANALYSIS SUPPORT APPARATUS, AND ANALYSIS SUPPORT METHOD

CROSS REFERENCE TO RELATED APPLICATION

This is a continuation application of PCT/JP2007/069314 filed on Oct. 2, 2007, the contents of which are incorporated herein by reference.

FIELD

The embodiment discussed herein is related to a computer product, an analysis support apparatus, and an analysis support method that support analysis of a biological phenomenon.

BACKGROUND

In the body of a living creature, i.e., in vivo, many chemical substances such as genes, proteins, lipids, and acids are present. These chemical substances are each present as molecules and affect one another. The mutual influence among molecules is referred to as "molecular interaction".

Because countless molecules are present in vivo, many molecular interactions naturally occur. A molecular interaction does not occur independently and a sequence of molecular interactions often occurs. For example, "molecule A affects molecule B and as a result, molecule B forms molecule C, i.e., the molecular interactions are linked to one another like a string of beads, starting from molecular A to molecular B and, then, to the molecular C. A group of molecular interactions linked in such a manner is referred to as a "pathway".

A pathway is useful in understanding biological processes. For example, "molecule C is deformed by a molecular interaction of molecule A and molecule B and as a result, the deformation of the molecule C causes a particular disorder"; "the structure of molecule C is maintained by a molecular interaction of molecule A and molecule B and as a result, normal organ function is continued".

As described in the above examples, an overview of biological processes, regardless of normal or abnormal function, becomes understandable through pathways of molecular interaction sequences. Therefore, building a pathway is important in biological science related fields such as in medical services and pharmaceutical development. There are a number of pathway building methods.

"Curation" is one method. "Curation" is a method of building a pathway, where a specialist called "curator" reads published literature, extracts portions that describe molecular interactions, and combines the molecular interactions to build the pathway.

Because curation is a method of building a pathway based on a human resource of curators, the amount of published literature to be read relates directly to work load. "PubMed" (see, e.g., Pubmed, available online on Sep. 24, 2007) is a website that discloses a database of published literature.

For reference, "KEGG" (see, e.g., KEGG: Kyoto Encyclopedia of Genes and Genomes, available online on Sep. 24, 2007), "BioCarta" (see, e.g., BioCarta, available online on Sep. 24, 2007), etc., are websites that disclose databases of pathways built by curation.

Data mining and text mining by mechanical processing are other examples of pathway building. "Data mining" is a generic name for knowledge finding approaches involving finding hidden relations and meanings by analyzing a large amount of data using various statistical analysis approaches. In particular, obtaining specific findings and ideas by dividing text data (ordinary, natural sentences) into words, etc., and analyzing the appearance frequencies of the words and correlations therebetween is referred to as "text mining".

The methods employed for specialized text mining in biotechnology include a method of building a pathway, where mechanical syntax analysis is executed on "molecules" that cause molecular interaction, an "action" that each of the molecules exerts, etc. and that are included in published literature and thereby, interactions are extracted to build a pathway. By combining text mining and data mining, pathways that are meaningful in terms of life sciences, e.g., "a pathway related to colon cancer" may be built by a computer.

"MeSH" (MeSH, available online on Sep. 24, 2007) are biological and medical terms used in biological data mining. MeSH stands for Medical Subject Headings and refers to a group of biological and medical terms. MeSH terms are already given to published literature and by calculating the total amount of the MeSH terms, it becomes possible to analyze the significance a particular group of published literature has biologically and medically.

Further, websites disclose a database formed by correlating biological and medical significance to molecules constituting a pathway. OMIM (see, e.g., OMIM, available online on Sep. 24, 2007) and H-invDB (see, e.g., H-inv DB, available online on Sep. 24, 2007) each correspond to such a website. Both databases are formed by correlating genetic significance to the molecules. The biological and medical significance of a molecule, a gene, etc. may be identified by using the data in each of these databases in data mining.

BioCreAtIvE (available online on Sep. 24, 2007) is a reference concerning text mining specialized for biology and pharmaceutical. "BioCreAtIvE" is a research organization. "HPRD" is a website that discloses a database having interaction information preliminarily stored therein (see, e.g., Human Protein Reference Database, available online on Sep. 24, 2007) and "BOND" is a website that provides data for a fee (see, e.g., BOND, available online on Sep. 24, 2007). These websites have registered therein direct interactions between proteins such as "bonding". Information on the molecular interactions registered therein may be collectively obtained and may be used for data mining, etc.

"ResNet" from ARIADNE GENOMICS, Inc., is a commercial database formed by correlating "types" and "functions" of molecules as the significance of a molecular interaction and the molecules that cause the molecular interaction. Such a database may be purchased and data mining may be executed using the database.

Combining the above text mining with data mining enables a computer to build a pathway significant in terms of life science, such as "pathway associated with colon cancer". Software having a function of numerically expressing the level of correlation between a medical/biochemical phenomenon, such as a disease, and a pathway built in such a manner is known. MetaCore, a product of US-based GeneGo Inc., is provided as such software (see MetaCore, available online on Sep. 24, 2007). It is not clear, however, whether MetaCore "numerically expresses the level of correlation between a molecular interaction described in a reference and MeSH" or "numerically expresses the level of correlation between a molecule described in a reference and MeSH".

Further, Japanese Laid-Open Patent Publication No. 2006-146380 introduces a conventional technique of giving "biological and medical" information concerning, for example, a disorder, to a molecular interaction. International Publication Pamphlet No. WO2003-077159 introduces a method of using a set of routes among two or more molecules called "subnet" as an approach of selecting a route that is selected taking into account the degree of relation to a disorder. Subnets each concern a disorder, etc., and are built in advance. When a route is sought, if a subnet concerning a disorder is hit, the selection of a route related to the disorder is enabled.

Japanese Laid-Open Patent Publication No. 2005-122231 discloses a method of displaying a screen to build a network of terms such as compounds concerning a gene, names of disorders, and proteins. This method is an approach where a user designates a term group 1 and a term group 2 to depict, as a network, information from published literature that suggest relations among the terms.

The discovery of a new role of a pharmaceutical leads to an extension of the term of patent right, which is industrially significant. Many pharmaceutical companies around the world are making aggressive efforts to extend the terms of patent rights. The discovery of a new role of a biological molecule such as gene is also academically and industrially beneficial. A method of advancing the discovery of a new role of a molecule, such as a pharmaceutical and gene, functioning in a living body, however, is not particularly found among the above conventional techniques disclosed in each of the cited Nonpatent Literatures and Patent Documents, in the field of pathway analysis.

The conventional technique disclosed in MetaCore, available online on Sep. 24, 2007, goes no further than suggesting a numerical correlation of a pathway brought about by an administered pharmaceutical or a deficient gene and a medical/biological phenomenon, such as "colon cancer", and does not promote the discovery of a new role played by a molecule, such as an administered pharmaceutical and deficient gene.

Japanese Laid-Open Patent Publication No. 2006-146380 does not offer a technique that promotes the discovery of a new role of an administered pharmaceutical, gene, etc. International Publication Pamphlet No. WO2003-077159 suggests a route of a pathway associated with a disease, but falls short of advancing the discovery of such a route, a new role of a pharmaceutical used in an experiment and a deficient gene.

With contributions to PubMed increasing at steady pace, biological research on biomolecular mechanisms is in constant progress and kept updated. As a result, a pre-built subnet fails to cover some biological/medical information. International Publication Pamphlet No. WO2003-077159, however, presents no alternative and makes no reference to a method of building a computer-based subnet related to diseases and continuously updatable, thus is regarded as insufficient.

Japanese Laid-Open Patent Publication No. 2005-122231 does not present a method of displaying correlations of molecules or inter-molecular links and the biological/medical significance of a chronic idiopathic disease, etc.

Databases giving biological/medical significance to genes, such as OMIM (OMIM, available online on Sep. 24, 2007) and H-invDB (H-inv DB, available online on Sep. 24, 2007), and databases storing interaction information, such as HPRD (Human Protein Reference Database, available online on Sep. 24, 2007) and BOND (BOND, available online on Sep. 24, 2007), are effective as materials for data mining, but have no function of building a pathway. Thus, this makes impossible the study of a biological phenomenon in a pharmaceutical experiment or a deficient gene test enabled by pathways and obviously, does not promote the discovery of a new role of a molecule from the experimental results.

Pathway analysis software, such as MetaCore from US-based GeneGo Inc. (MetaCore, available online on Sep. 24, 2007), offers no function of promoting the discovery of a new role played by a molecule, such as a pharmaceutical and gene, using a pharmaceutical and a deficient gene used in an experiment and a pathway produced as a result of the experiment.

In this manner, the cited Nonpatent Literatures and Patent Documents do not lead to the promotion of discovery of a new role of a pharmaceutical and gene used in an experiment, from a pathway produced as a result of experiment, thus leave an unsolved problem.

The present invention was conceived in view of the above circumstances, and it is therefore an object of the present invention to provide an analysis support program, an analysis support apparatus, and an analysis support method that search for a new role of a molecule to contribute to a reduction in burden on a user, the promotion of new pharmaceutical research/development, and extension of term of patent right.

SUMMARY

According to an aspect of an embodiment, a computer-readable recording medium stores therein an analysis support program that causes a computer to execute receiving test result data identifying a molecule administered to a test subject or a deficient molecule, as an analysis subject molecule, and quantity-changing molecules that have changed in quantity due to administration or deficiency of the analysis subject molecule in the test subject; acquiring a first pathway indicating an interaction between the quantity-changing molecules identified by the test result data; acquiring a second pathway indicating a molecular interaction with the analysis subject molecule, from a database storing therein for each molecular interaction, a type; determining from among biological phenomena correlated with the interaction between quantity-changing molecules of the first pathway, determines a biological phenomenon other than a biological phenomenon correlated with a molecular interaction of the second pathway to be a novel biological phenomenon caused by administration or deficiency of the analysis subject molecule; and outputting a determination result obtained at the determining.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is an explanatory diagram of the storage content of a medical reference DB.

FIG. 7 is an explanatory diagram of an example of test result data.

FIG. 8 is an explanatory diagram of an integrated table.

FIG. 21 is another flowchart of the analysis support procedure by the server.

DESCRIPTION OF EMBODIMENTS

Preferred embodiments of the present invention will be explained with reference to the accompanying drawings. An overview of the embodiment will be described first. In the present embodiment, molecules, such as protein, as well as pharmaceuticals, genes, and compounds are collectively referred to as "molecule". To discover a new role of a molecule, it is necessary to organize information reported on the molecule as known information, to compare the known information against information acquired from experimental results, and from the result of comparison, to select what is unknown, i.e., a new role of the molecule.

Figure 1:
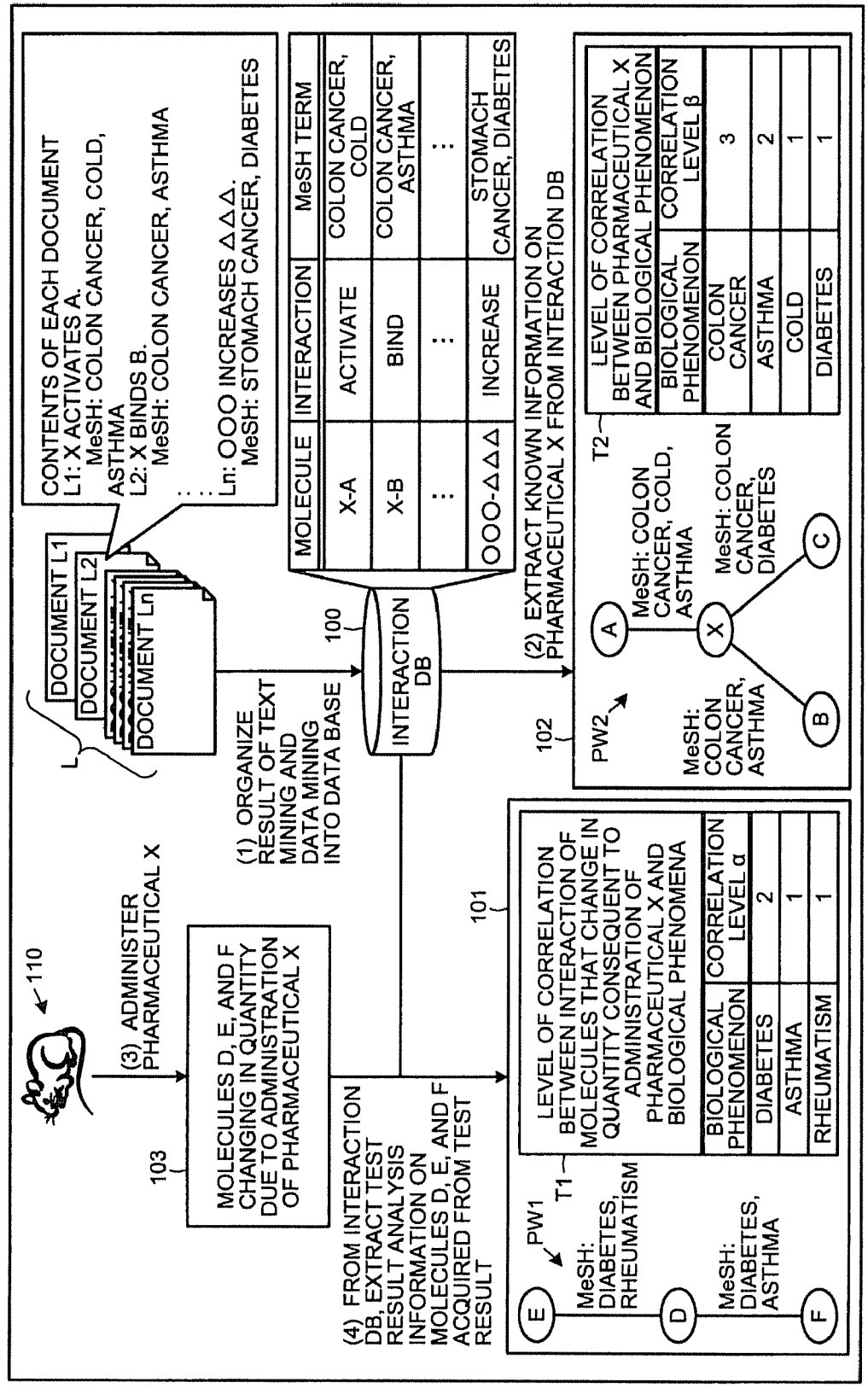
FIG. 1 is a schematic of molecular analysis according to an embodiment.

FIG. 1 is a schematic of molecular analysis according to the embodiment. In FIG. 1, known information of a medical reference group L is used. Molecular interactions and MeSH terms are described in references L1 to Ln. In the reference L1, for example, molecules X and A and a molecular interaction representing activation ("activate") are described in a form such as "X activate A". In addition, MeSH terms "colon cancer", "cold", and "asthma" are assigned in the reference L1.

(1) First, the medical reference group L is subjected to text mining and data mining, and the result of the text mining and data mining is organized into information in the form of a database called interaction DB 100. The interaction DB 100 stores, for each molecular interaction, the type of molecular interaction (e.g., "activate") and MeSH terms (e.g., "colon cancer").

(2) When a pharmaceutical X is to be examined, the interaction DB 100 is accessed and using the pharmaceutical X as a key, known information 102 concerning the pharmaceutical X from the interaction DB 100 is extracted. The known information 102 includes a pathway PW2 centered on the pharmaceutical X and a correlation level table T2 indicating the strength of correlation between the pharmaceutical X and biological phenomena. A correlation level is determined, for example, by counting the frequency of appearance of MeSH terms. A correlation level can also be calculated by various statistical methods.

The pathway PW2 is a molecular network centered on the pharmaceutical X. Specifically, the pathway PW2 is made up of molecules A, B, and C molecularly interacting directly with the pharmaceutical X, a molecular interaction between the molecule X and the molecule A, a molecular interaction between the molecule X and the molecule B, and a molecular interaction between the molecule X and the molecule C (each molecular interaction being represented by a line segment connecting the molecules). Since MeSH terms are assigned to each molecular interaction, a sum of the assigned MeSH terms gives numerical values representing correlation levels indicated in the correlation level table T2.

Although here, the pathway PW2 includes only the extracted molecules molecularly interacting directly with the pharmaceutical X, other molecules molecularly interacting with the molecules interacting directly with the pharmaceutical X, that is, molecules indirectly linked to the pharmaceutical X may also be included in the pathway PW2. The extent to which the pathway PW2 is expanded can be determined arbitrarily by the user.

In this manner, the known information 102 includes references related to colon cancer, which is correlated with interactions "pharmaceutical X-molecule A", "pharmaceutical X-molecule B", and "pharmaceutical X-molecule C", indicating that the pharmaceutical X is correlated highest with colon cancer. In contrast, a reference related to diabetes is correlated with only one interaction "pharmaceutical X-molecule C", indicating that the pharmaceutical X has a low correlation with diabetes.

Accessing a reference serving as the basis for a correlation level enables confirmation of the contents of the reference, i.e., both numerical value tendency and the contents related to a biological phenomenon of a molecule are classified as the known information 102.

Adding, as an information source, the results of an experiment that uses the same pharmaceutical X also enables the building of a pathway. Using experimental results enables correlation of medical/biological significance and the administered pharmaceutical X. Although, here, the molecule X is given as a pharmaceutical, the molecule X may be a knock-out/knock-down (congenitally or postnatally deficient) gene, enabling correlation of medical/biological significance and the deficient gene. A test depicted in FIG. 1 is a case where the pharmaceutical X is administered to a mouse, which is a test subject 110.

(3) In this test, the pharmaceutical X is administered to the test subject 110 and a test result 103 is acquired. In the test result 103, molecules D, E, F having changed in quantity due to the administration of the pharmaceutical X are obtained from among an enormous number of molecules. (4) The interaction DB 100 is accessed and the molecules D, E, F obtained from the test result 103 are searched for to extract test result analysis information 101 concerning the pharmaceutical X.

A pathway PW1 in the test result analysis information 101 is a molecular network related to molecules that have changed in quantity as a result of the administration of the pharmaceutical X. The molecular network includes the molecules D, E, F acquired from the test result 103 and molecular interactions interlinking the molecules D, E, and F. Because the molecules D, E, and F that emerge are bound by the test result 103, this molecular network reflects the test result 103.

In a correlation level table T1 in the test result analysis information 101, the strength of correlation between an interaction of the molecules having changed in quantity due to administration of the pharmaceutical X and a biological phenomenon is expressed as a correlation level. A correlation level is determined, for example, by counting the frequency of appearance of a MeSH term assigned to an interaction (which is expressed as a line segment linking molecules) between molecules that have changed in quantity. A correlation level can also be calculated by various statistical methods.

Different from the known information 102 indicating a high correlation with colon cancer, the test result analysis information 101 indicates the highest correlation with diabetes. Interactions between molecules changing quantity and correlated with diabetes are found to be "molecule D-molecule E" and "molecule D-molecule F", and the pharmaceutical X does not appear in the pathway PW1.

Comparison of the information 101 and 102 enables the following observation. While the correlation of the pharmaceutical X and diabetes seems to be low according to the known information 102, the test result analysis information 101, obtained from an actual test to analyze the molecules D, E, and F changing in quantity, indicates that diabetes has the highest correlation with the administration of the pharmaceutical X.

The test result analysis information 101 indicates that the molecules D, E, and F changing in quantity are correlated with diabetes while the molecules D, E, and F are not indicated by the known information 102 concerning the pharmaceutical X, presenting a completely new role of the pharmaceutical X, i.e., "the molecules E, D, and F are affected by administration of the pharmaceutical X, the consequence of which is correlated with diabetes", which is not indicated by the known information 102.

"Rheumatism" appears in the test result analysis information 101, but a reference concerning symptoms of "rheumatism" is not present in the known information 102 concerning the pharmaceutical X, presenting a new role of the pharmaceutical X, i.e., "the molecules D and E are affected by administration of the pharmaceutical X, the consequence of which is correlated with rheumatism". This new role offers high novelty not only on a molecular level but also on a symptomatic level. The present embodiment provides a technique that presents a new role of the pharmaceutical X. The embodiment will hereinafter be described in detail.

Figure 2:
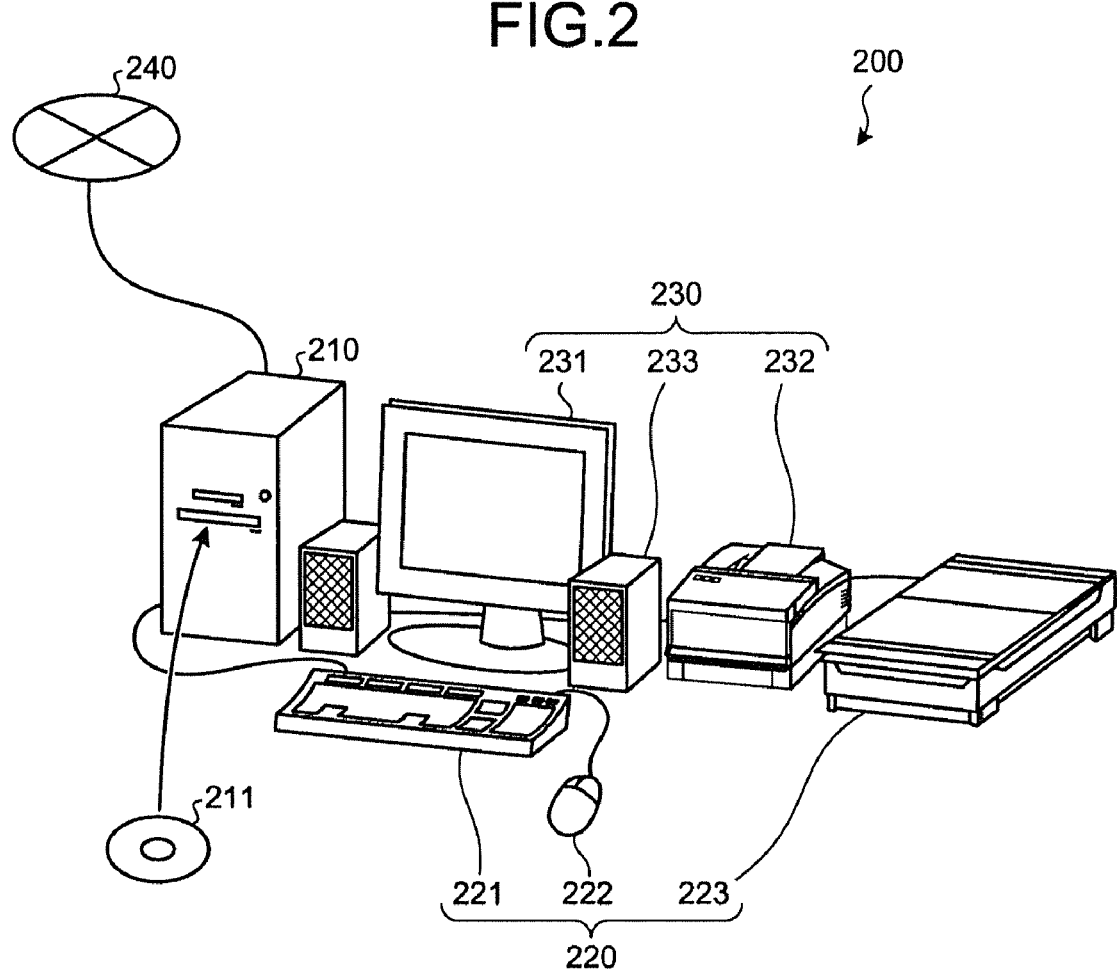
FIG. 2 is a diagram for explaining a hardware configuration of an analysis support apparatus according to the embodiment of the present invention.

First, hardware configuration of an analysis support apparatus according to the embodiment of the present invention will be described. FIG. 2 is a diagram for explaining a hardware configuration of the analysis support apparatus according to the embodiment of the present invention.

As depicted in FIG. 2, an analysis support apparatus 200 includes a computer 210, an input device 220, and an output device 230, connectable to a network 240, e.g., a LAN, a WAN, or the Internet through a non-depicted router or a modem.

The computer 210 has a CPU, a storage unit, and an interface. The CPU governs overall control of the analysis support apparatus 200. A storage unit is formed of, for example, a ROM, a RAM, a HD, an optical disk 211, or a flash memory. The RAM is used as a work area of the CPU.

Various programs are stored in the storage unit and loaded in response to a command from the CPU. The reading and the writing of data with respect to the HD and the optical disk 211 are controlled by a disk drive. The optical disk 211 and the flash memory are removable from the computer 210. The interface controls input from the input device 220, output to the output device 230, and transmission/reception with respect to the network 240.

As the input device 220, a keyboard 221, a mouse 222, and a scanner 223 are adopted. The keyboard 221 includes keys to input, for example, characters, numeric figures, and various kinds of instructions, and data is input through the keyboard 221. The keyboard 221 may be a touch panel. The mouse 222 is used to move a cursor, select a range, move a window, or change window size. The scanner 223 optically reads an image as image data, which is stored in the storage unit of the computer 210. The scanner 223 may have an OCR function.

As the output device 230, a display 231, a printer 232, a speaker 233, etc. are adopted. The display 231 displays a cursor, an icon, or a tool box as well as data, such as text, an image, and function information. The printer 232 prints image data or text data. The speaker 232 outputs sound, e.g., a sound effect or a text-to-voice converted sound.

The storage content of a medical reference DB used by the analysis support apparatus 200 according to the present embodiment will be described. FIG. 3 is an explanatory diagram of the storage content of the medical reference DB used by the analysis support apparatus 200 according to the present embodiment. As depicted in FIG. 3, a medical reference DB 300 is a database that is open to the public and for each reference ID identifying a medical reference, stores therein the title, the abstract (summary), the author(s), the date of publication, and the MeSH terms of the medical reference. "MeSH terms" are biological and medical terms that are used for searching a reference. The biological and medical significance that a specific group of medical references has may be analyzed by statistical calculation of MeSH terms assigned to the medical references.

A function of the medical reference DB 300 is implemented by a recording medium such as an HD or a semiconductor memory. The medical reference DB 300 may be incorporated in the analysis support apparatus 200 or may be accessed by the analysis support apparatus 200 from an external server through the network 240.

Figure 4:
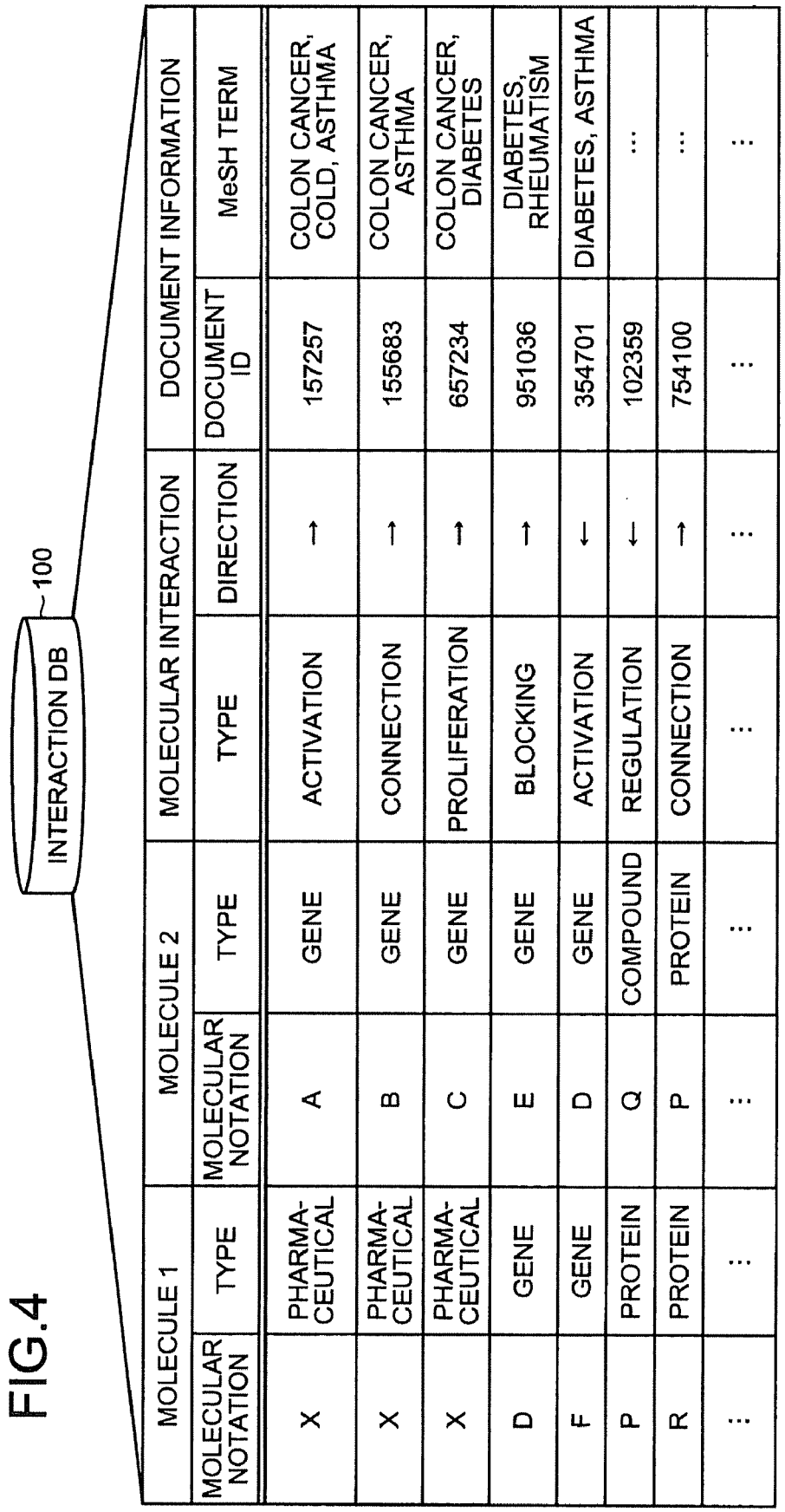
FIG. 4 is an explanatory diagram of the storage content of an interaction DB.

The storage content of the interaction DB 100 will be described. FIG. 4 is an explanatory diagram of the storage content of the interaction DB 100. As depicted in FIG. 4, the interaction DB 100 stores in each record, the molecular notation and type of a molecule 1, the molecular notation and type of a molecule 2, the type and direction of a molecular interaction, and reference information (reference ID and MeSH term) and thus, a molecular interaction is specified for each record.

The molecule 1 is the molecule at one end of a molecular interaction and the molecular 2 is the molecule at the other end of the interaction. The molecular notation is a notation representing a molecule making up a molecular interaction. The type (of molecule) means the type of molecule (protein, compound, gene, pharmaceutical, etc.) making up a molecular interaction.

The type (of molecular interaction) means the type of molecular interaction (blocking, connection, activation, etc.) between molecules (molecules 1 and 2). The direction (of molecular interaction) is information indicating whether a molecule identifying a molecular interaction is the affected molecule or the effecting molecule. For example, the direction of a molecular interaction given as "→" indicates that the molecule 1 affects the molecule 2 in the interaction. The reference ID is the ID of the medical document describing a molecule identifying a molecular interaction. The interaction DB 100 is linked to the medical reference DB 300 via the reference ID. The MeSH term is a biomedical term that is used for a reference search.

Molecular interactions are identified according record, by the molecular notation and type of the molecule 1, the molecular notation and type of the molecule 2, the type and direction of the molecular interaction, and the reference information (reference ID and MeSH term). A molecular interaction is built with information extracted by syntax analysis through curation, natural language processing, etc.

A function of the interaction DB 100 is implemented by a recording medium such as an HD or a semiconductor memory. The interaction DB 100 may be incorporated in the analysis support apparatus 200 or may be accessed by the analysis support apparatus 100 from an external server through the network 140.

Figures 5, 6:
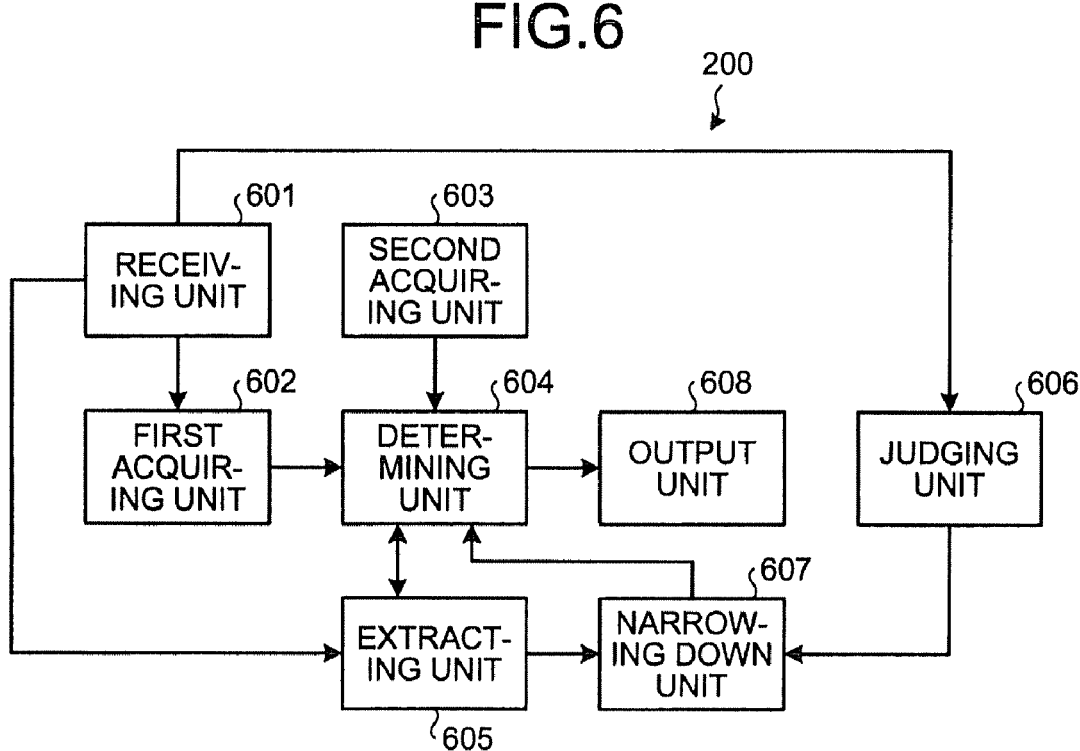
FIG. 5 is an explanatory diagram of the storage content of a quantity-changing pattern.
FIG. 6 is a block diagram of a functional configuration of the analysis support apparatus.

The storage content of a quantity-changing pattern DB will be described. FIG. 5 is an explanatory diagram of the storage content of the quantity-changing pattern DB. As depicted in FIG. 5, a quantity-changing pattern identifies an increase/decrease in the quantity of quantity-changing molecules. For example, a pattern P2 indicates that the quantity-changing molecules D and F decrease while the quantity-changing molecule E increases. The quantity-changing pattern DB 500 is built using test results measuring an increase/decrease in molecules in a living body.

A function of the quantity-changing pattern DB 500 is implemented by a recording medium such as a HD and semiconductor memory. The quantity-changing pattern DB 500 may be incorporated in the analysis support apparatus 200 or may be made accessed by the analysis support apparatus 200 from an external server via the network 240.

A functional configuration of the analysis support apparatus 200 will be described. FIG. 6 is a block diagram of a functional configuration of the analysis support apparatus 200. In FIG. 6, the analysis support apparatus 200 includes a receiving unit 601, a first acquiring unit 602, a second acquiring unit 603, a determining unit 604, an extracting unit 605, a judging unit 606, a narrowing down unit 607, and an output unit 608. These functional units 601 to 608 are implemented by causing the CPU to execute relevant programs stored in a storage unit or through the input/output I/F.

Data output from the functional units 601 to 608 is stored in a memory. Functional units at connection destinations indicated by arrows in FIG. 6 are implemented by causing the CPU to read from the storage unit, data output from a functional unit at the corresponding connection origin and to execute a relevant program.

The receiving unit 601 has a function of receiving test result data identifying a molecule administered to the test subject 110 or a deficient molecule (analysis subject molecule), and quantity-changing molecules in the test subject 110 that have changed in quantity as a result of administration or a deficiency of the analysis subject molecule. Test result data will be described.

FIG. 7 is an explanatory diagram of an example of test result data. In FIG. 7, test result data 700 identifies an analysis subject molecule, quantity-changing molecules that have changed in quantity as a result of administration (or a deficiency) of the analysis subject molecule, and quantities before and after the administration (or deficiency).

For example, in the case of the quantity-changing molecule D, if the relation between the pre-administration quantity Qd and the post-administration quantity QD is Qd<QD, it indicates that the quantity-changing molecule D increases as a result of administration of the pharmaceutical X. In the same manner, the relation of Qd>QD indicates that the quantity-changing molecule D decreases as a result of administration of the pharmaceutical X, and the relation of Qd=QD indicates that the quantity-changing molecule D does not change in quantity in spite of administration of the pharmaceutical X. The same observation applies to cases of the quantity-changing molecules E and F.

Methods of measuring a change in quantity include, for example, a method of microarray for measuring changes in gene expression. In addition to methods for measuring genes, methods for measuring protein and other chemical substances are also provided and include, for example, nuclear magnetic resonance (NMR), magnetic resonance imaging system (MRI), and mass spectrometry.

The receiving unit 601 may be configured to receive input of the test result data 700 by user operation of a keyboard, mouse, etc., or to call up the test result data 700 stored in the storage unit, or to receive the test result data 700 from an external computer via the network 240. The receiving unit 601 receives various types of information, such as specification information specifying a biological phenomenon, in addition to the test result data 700.

The first acquiring unit 602 has a function of acquiring a first pathway indicating interactions between quantity-changing molecules identified by the test result data 700 received by the receiving unit 601. In the case of the test result data 700 of FIG. 7, for example, the pathway PW1 is acquired as the first pathway based on the quantity-changing molecules D, E, F.

According to a method of acquiring the pathway PW1, the interaction DB 100 is searched, using the quantity-changing molecules D, E, F as keys, to extract interactions between quantity-changing molecules D, E, F, and interactions between the quantity-changing molecules are represented as links to build the pathway PW1. A MeSH term is assigned to each of the interactions between the quantity-changing molecules.

The first acquiring unit 602 also acquires the first correlation level of each biological phenomenon correlated with an interaction between quantity-changing molecules of the first pathway. For example, when the first pathway is the pathway PW1, the first acquiring unit 602 acquires the correlation level table T1 of FIG. 1. Correlation level $\alpha$ in the correlation level table T1 corresponds to the first correlation level.

In the present embodiment, the correlation level $\alpha$ being taken into the analysis support apparatus 200 suffices for the embodiment. The analysis support apparatus 200 may analyze the acquired pathway PW1 and statistically calculate the correlation level $\alpha$ using MeSH terms (e.g., counting the number of MeSH terms), or may receive the correlation level $\alpha$ (or correlation level table T1) calculated by an external computer.

The second acquiring unit 603 has a function of acquiring a second pathway indicating molecular interactions with an analysis subject molecule. For example, in the case of the known information 102 of FIG. 1, the pathway PW2 is acquired as the second pathway based on the interaction DB 100, using the molecules X, A, B, C.

According to a method of acquiring the pathway PW2, the interaction DB 100 is searched using the pharmaceutical X as a key, to extract molecular interactions of molecules A, B, C, interacting molecularly with the pharmaceutical X, and the extracted molecular interactions are represented by links to build the pathway PW2. A MeSH term is assigned to each of the molecular interactions.

The second acquiring unit 603 also acquires the second correlation level of each biological phenomenon correlated with the molecular interactions indicated in the second pathway. For example, when the second pathway is the pathway PW2, the second acquiring unit 603 acquires the correlation level table T2 of FIG. 1. Correlation level $\beta$ in the correlation level table T2 corresponds to the second correlation level.

In the present embodiment, the correlation level $\beta$ being taken into the analysis support apparatus 200 suffices for the embodiment. The analysis support apparatus 200 may analyze the acquired pathway PW2 and statistically calculate the correlation level $\beta$ using MeSH terms (e.g., counting the number of MeSH terms), or may receive the correlation level β (or correlation level table T2) calculated by an external computer.

The determining unit 604 has a function of determining, from among biological phenomena correlated with interactions between quantity-changing molecules of the first pathway, a biological phenomenon other than a biological phenomenon correlated with a molecular interaction of the second pathway to be a novel biological phenomenon caused by administration or deficiency of an analysis subject molecule. "Novel biological phenomenon" means a biological phenomenon that cannot be acquired from the second pathway and also means a biological phenomenon that can be acquired from the second pathway but is downplayed in the second pathway. For example, "diabetes", "asthma", and "rheumatism", which are biological phenomena correlated with interactions between quantity-changing molecules of the pathway PW1, make up a population for a determining process.

A biological phenomenon other than "colon cancer", "asthma", "cold", and "diabetes", which are biological phenomena correlated with molecular interactions of the pathway PW2, is selected from the population. In this case, the selected biological phenomenon is "rheumatism". The determining unit 604 thus determines "rheumatism" to be a novel biological phenomenon caused by administration of the pharmaceutical X. The correlation of the pharmaceutical X and rheumatism is not found at all by reference of the pathway PW2 using the pharmaceutical X as a key or by reference of the correlation level table T2. Through the present embodiment, however, it becomes known that the pharmaceutical X is closely associated not with "colon cancer" but actually with "rheumatism". This leads to the discovery of a new role of the pharmaceutical X.

In this manner, not only a biological phenomenon in the correlation level table T1 is selected, but biological phenomena in the correlation level table T2 are also subject to determination. For example, the correlation levels α and β of a given biological phenomenon in the correlation level tables T1 and T2 are compared, and the biological phenomenon may be regarded as a novel phenomenon depending on the result of the comparison.

In this case, the correlation level tables T1 and T2 are integrated into one table. FIG. 8 is an explanatory diagram of an integrated table. In FIG. 8, a ratio is a value given by $\alpha/\beta$. When $0 \leq \alpha/\beta \leq 1$, which means $\alpha \leq \beta$, is satisfied for a given biological phenomenon, it means that the biological phenomenon has strong correlation with the pharmaceutical X but weak correlation with the administration of the pharmaceutical X. The biological phenomenon is, therefore, not regarded as a novel phenomenon. In the case of FIG. 8, "asthma" and "cold" are not regarded as novel phenomena. In the pathway PW2 and the correlation level table T2, "colon cancer" having the highest correlation level is not regarded as a novel phenomenon.

When $\alpha/\beta > 1$, which means $\alpha > \beta$, is satisfied for a given biological phenomenon, it means that the biological phenomenon has weak correlation with the pharmaceutical X but strong correlation with the administration of the pharmaceutical X. The biological phenomenon is, therefore, regarded as a novel phenomenon. In the example of FIG. 8, "rheumatism" as well as "diabetes" having the lowest correlation level in the pathway PW2 and in the correlation table T2 are determined to be novel biological phenomena caused by administration of the pharmaceutical X. Although "diabetes" is assigned as a MeSH term to an interaction in the pathway PW1, "diabetes" is neglected in the pathway PW2 in which "colon cancer" is regarded as important. Through comparative evaluation based on the correlation levels α and β, however, "diabetes" as a biological phenomenon downplayed in the PW2 can be determined to be a biological phenomenon higher in novelty than "colon cancer" regarded as important in the pathway PW2.

The determining unit 604 determines a novel biological phenomenon and then determines a novel pathway using the novel biological phenomenon as a key. The determining unit 604, however, may determine a novel pathway without determining a novel biological phenomenon. In such a case, the extracting unit 605 extracts from the pathway PW1, a pathway indicating an interaction that is between quantity-changing molecules and correlated with a biological phenomenon other than a biological phenomenon correlated with molecular interactions of the pathway PW2. The determining unit 604 then determines the extracted pathway to be a novel pathway.

The output unit 608 has a function of outputting a determination result obtained by the determining unit 604. For example, the output unit 608 outputs the determination result in the form of display on a display screen, printout by a printer, or transmission to a computer requesting the determined result. In the case of transmission, the determination result is transmitted in a format that can be displayed on an OS, browser, or application program of the computer receiving the transmitted result. An example of a display format will be described.

Figure 9:
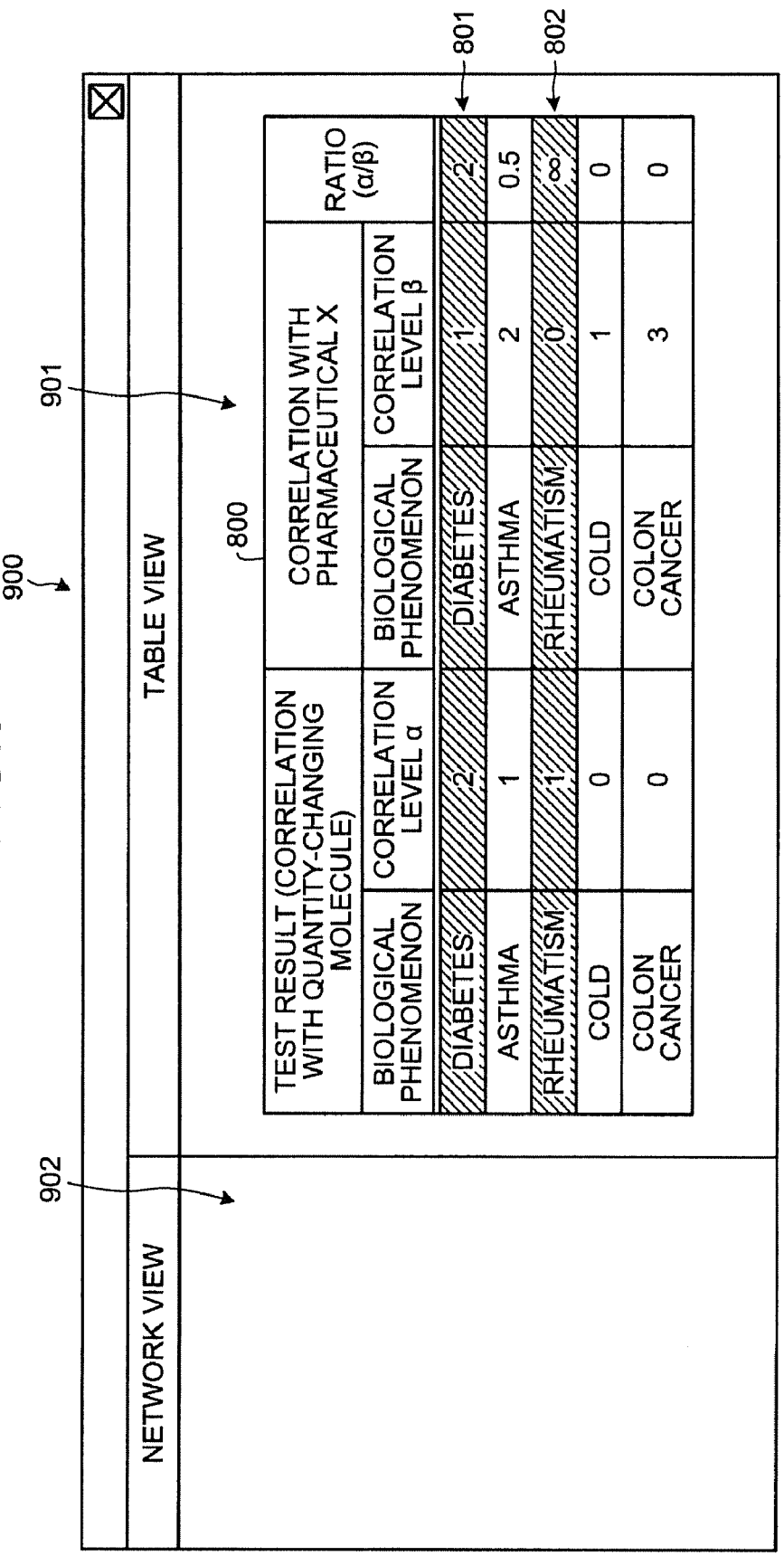
FIG. 9 is an explanatory diagram of a display example of a determination result.

FIG. 9 is an explanatory diagram of a display example of a determination result. In FIG. 9, the integrated table 800 of FIG. 8 is displayed in a table view area 901 on a display screen 900. Cells 801 and 802 of novel biological phenomena affected by administration of the pharmaceutical X are displayed in a highlighted state (hatched area in FIG. 9). This allows the user to visually recognize which biological phenomenon is a novel biological phenomenon affected by administration of the pharmaceutical X.

The extracting unit 605 has a function of extracting from the first pathway, a pathway indicating molecular interactions correlated with a biological phenomenon determined to be novel by the determining unit 604. In the example of FIG. 9, "diabetes" and "rheumatism" are determined to be novel biological phenomena. In the case of "diabetes", reference to the pathway PW1 of FIG. 1 reveals that "diabetes" is assigned as a MeSH term to an interaction between the quantity-changing molecules D and E and also to an interaction between the quantity-changing molecules D and F. In the case of "diabetes", therefore, the pathway PW1 is extracted directly.

In this case, the determining unit 604 determines the extracted pathway to be a novel pathway caused by administration (or deficiency) of the analysis subject molecule. Therefore, in this example, the determining unit 604 determines the pathway PW1 to be a novel pathway caused by administration of the pharmaceutical X.

The output unit 608 outputs the pathway PW1 determined to be a novel pathway. For example, the pathway PW1 is displayed in the network view area 902 on the display screen 900.

Figure 10:
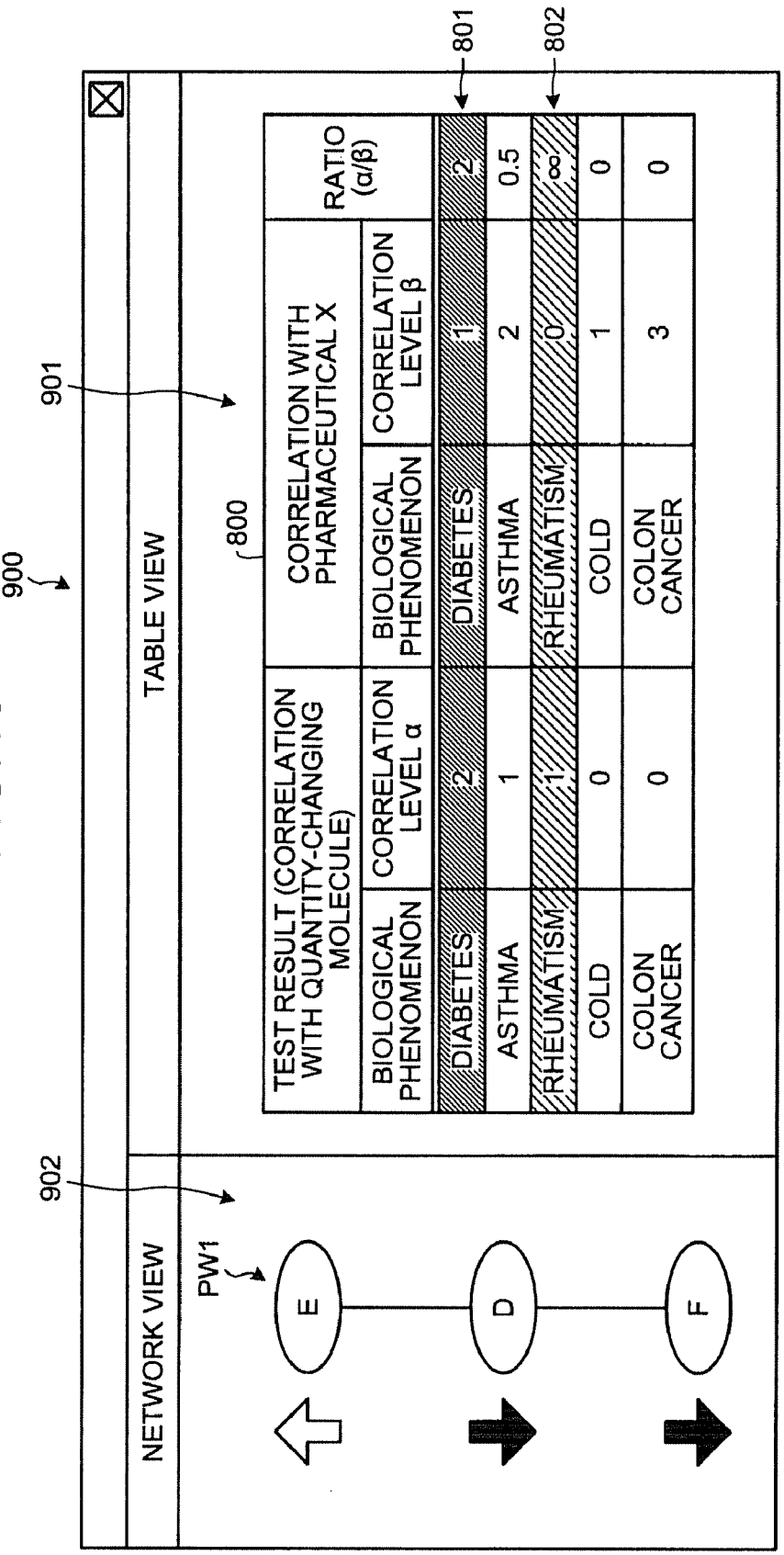
FIG. 10 is an explanatory diagram of a display example of a novel pathway PW1.

FIG. 10 is an explanatory diagram of a display example of the novel pathway PW1. In this example, the cell 801 of the biological phenomenon "diabetes" correlated with the pathway PW1 displayed in the network view area 902 is displayed in a highlighted state distinguishing the cell 801 from the cell 802 of "rheumatism" also displayed in a highlighted state in the integrated table 800.

In the case of "rheumatism", reference to the pathway PW1 of FIG. 1 reveals that "rheumatism" is assigned as a MeSH term to only the interaction between quantity-changing molecules D and E. As a result, a pathway indicating the interaction between the quantity-changing molecules D and E correlated with "rheumatism" is extracted from the pathway PW1.

In the case of "rheumatism", therefore, the pathway extracted from the pathway PW1 is determined to be a novel pathway by the determining unit 604. The output unit 608 thus outputs the pathway determined to have a novel function (part of the pathway PW1). For example, the pathway is displayed in the network view area 902 on the display screen 900.

Figure 11:
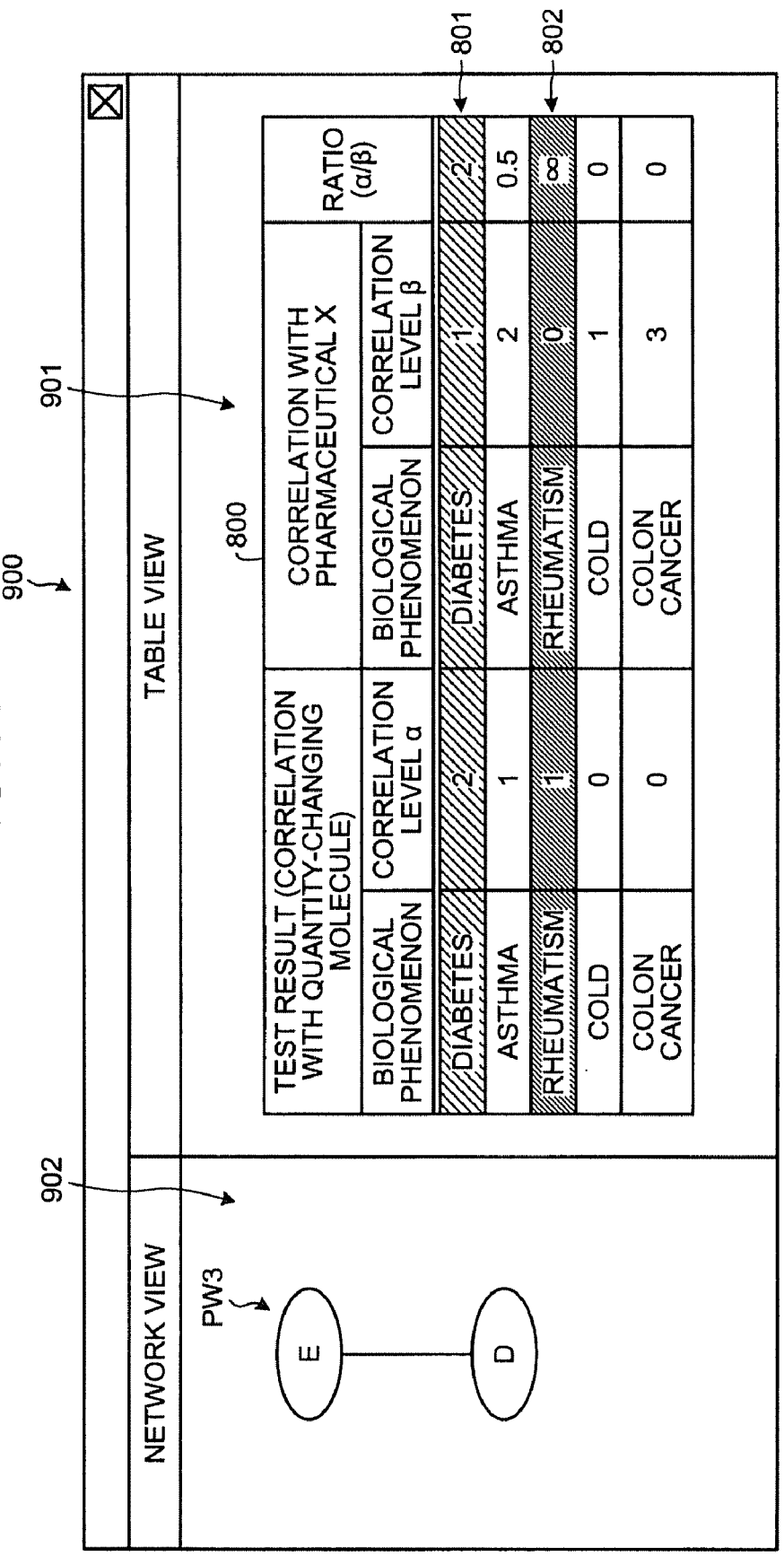
FIG. 11 is an explanatory diagram of a display example of a novel pathway PW3.

FIG. 11 is an explanatory diagram of a display example of a novel pathway PW3. In this example, the cell 802 of the biological phenomenon "rheumatism" correlated with the pathway PW3 displayed in the network view area 902 is displayed in a highlighted state distinguishing the cell 802 from the cell 801 of "diabetes" also displayed in a highlighted state in the integrated table 800.

The judging unit 606 has a function of judging whether quantity-changing molecules show a quantity-changing pattern identical (or similar) to a known quantity-changing pattern, based on information identifying a change in quantity for each quantity-changing molecule. Because the test result data 700 includes information identifying a change in quantity for each quantity-changing molecule, e.g., information of quantities before and after administration, whether a quantity-changing pattern is identical (or similar) to a known quantity-changing pattern can be judged by referring to the quantity-changing pattern DB 500.

For example, in the test result data 700 of FIG. 7, when Qd>QD (decrease) is satisfied for the quantity-changing molecule D, Qe>QE (increase) is satisfied for the quantity-changing molecule E, and Qf>QF (decrease) is satisfied for the quantity-changing molecule F, whether a combination of these molecules (D, E, F) and the quantity-changing pattern (decrease, increase, decrease) thereof are identical (or similar) to a known combination and pattern is judged.

Identicalness (or similarity) is judged in such a way that, for example, if a quantity-changing pattern in the test result data 700 completely matches a known quantity-changing pattern, the test result quantity-changing pattern is judged to be identical. For example, the pattern P2 of FIG. 5 completely matches the test result quantity-changing pattern, hence the test result quantity-changing pattern is judged to be identical.

When the test result quantity-changing pattern completely disagrees with a known pattern or the same combination of molecules is not present, the test result quantity-changing pattern is judged to be dissimilar. For example, the pattern P3 of FIG. 5 completely disagrees with the test result quantity-changing pattern, hence the test result quantity-changing pattern is judged to be dissimilar. When a quantity-changing pattern in the test result data 700 partially disagrees with a known quantity-changing pattern, similarity is judged based on the ratio of partial matching. For example, because three quantity-changing molecules are present in this example, the test result quantity-changing pattern is judged to be similar when two molecules match in pattern, but is judged to be dissimilar when only one molecule matches in pattern. For example, the pattern P1 of FIG. 5 matches the test result quantity-changing pattern only at the quantity-changing molecule E, so the test result quantity-changing pattern is judged to be dissimilar.

The narrowing down unit 607 has a function of narrowing down pathways extracted by the extracting unit 605, based on a judgment result obtained by the judging unit 606. For example, when multiple pathways are extracted by the extracting unit 605, each pathway is novel but certainty is unclear. Extracted pathways are thus narrowed down to a pathway judged to be identical or similar through judgment concerning quantity-changing patterns to add an element of certainty.

For example, the pathway PW1 correlated with "diabetes" and the pathway PW3 correlated with "rheumatism" are extracted in the above example. A quantity-changing pattern of the quantity-changing molecules D, E, and F making up the pathway PW1 correlated with "diabetes" is judged to be identical to the pattern P2 depicted in FIG. 5. If a known quantity-changing pattern identical to or similar to a quantity-changing pattern of the quantity-changing molecules D and E making up the pathway P3 correlated with "rheumatism" is not present, the pathway PW3 is excluded. Hence, the extracted pathways are narrowed down from the pathways PW1 and PW3 to the pathway PW1.

In this case, the determining unit 604 determines the narrowed down pathway PW1 to be a novel pathway. The output unit 608 then outputs the determined pathway by, for example, displaying the pathway in the network view area 902, as depicted in FIG. 10. In this case, an arrow is displayed near each molecule as information identifying a quantity-changing pattern. An upward arrow indicates an increase in quantity, while a downward arrow indicates a decrease in quantity.

Figure 12:
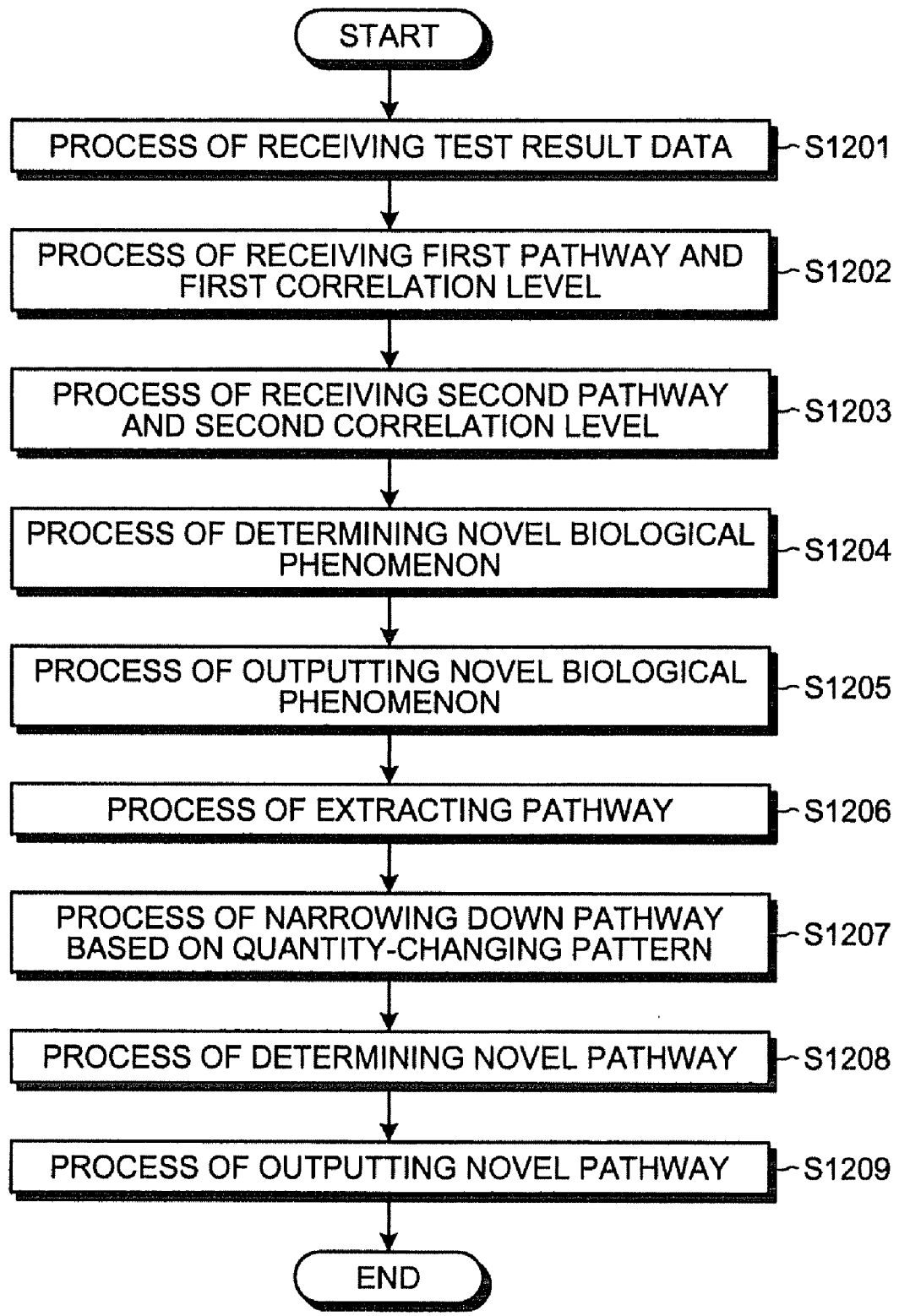
FIG. 12 is a flowchart of an analysis support procedure by the analysis support apparatus.

An analysis support procedure by the above analysis support apparatus will be described. FIG. 12 is a flowchart of the analysis support procedure by the analysis support apparatus. In FIG. 12, the receiving unit 601 executes a process of receiving the test result data 700 (step S1201). The first acquiring unit 602 executes a process of acquiring the first pathway (pathway PW1) and the first correlation level (correlation level table T1) (step S1202).

The second acquiring unit 603 executes a process of acquiring the second pathway (pathway PW2) and the second correlation level (correlation level table T2) (step S1203). Either one of these two acquiring processes may be executed first followed by the other, or both may be executed simultaneously.

Subsequently, the determining unit 604 executes a process of determining a novel biological phenomenon (step S1204), and the output unit 608 executes a process of outputting the novel biological phenomenon (step S1205). The extracting unit 605 executes a pathway extracting process (step S1206), and the narrowing down unit 607 executes a pathway narrowing down process based on quantity-changing patterns (step S1207). This narrowing down process is arbitrary.

The determining unit 604 executes a process of determining a novel pathway (step S1208), and the output unit 608 executes a process of outputting the novel pathway (step S1209), ending a series of processes. Through this procedure, a new role of a molecule can be discovered. Examples of the above embodiment will be described hereinafter.

Figure 13:
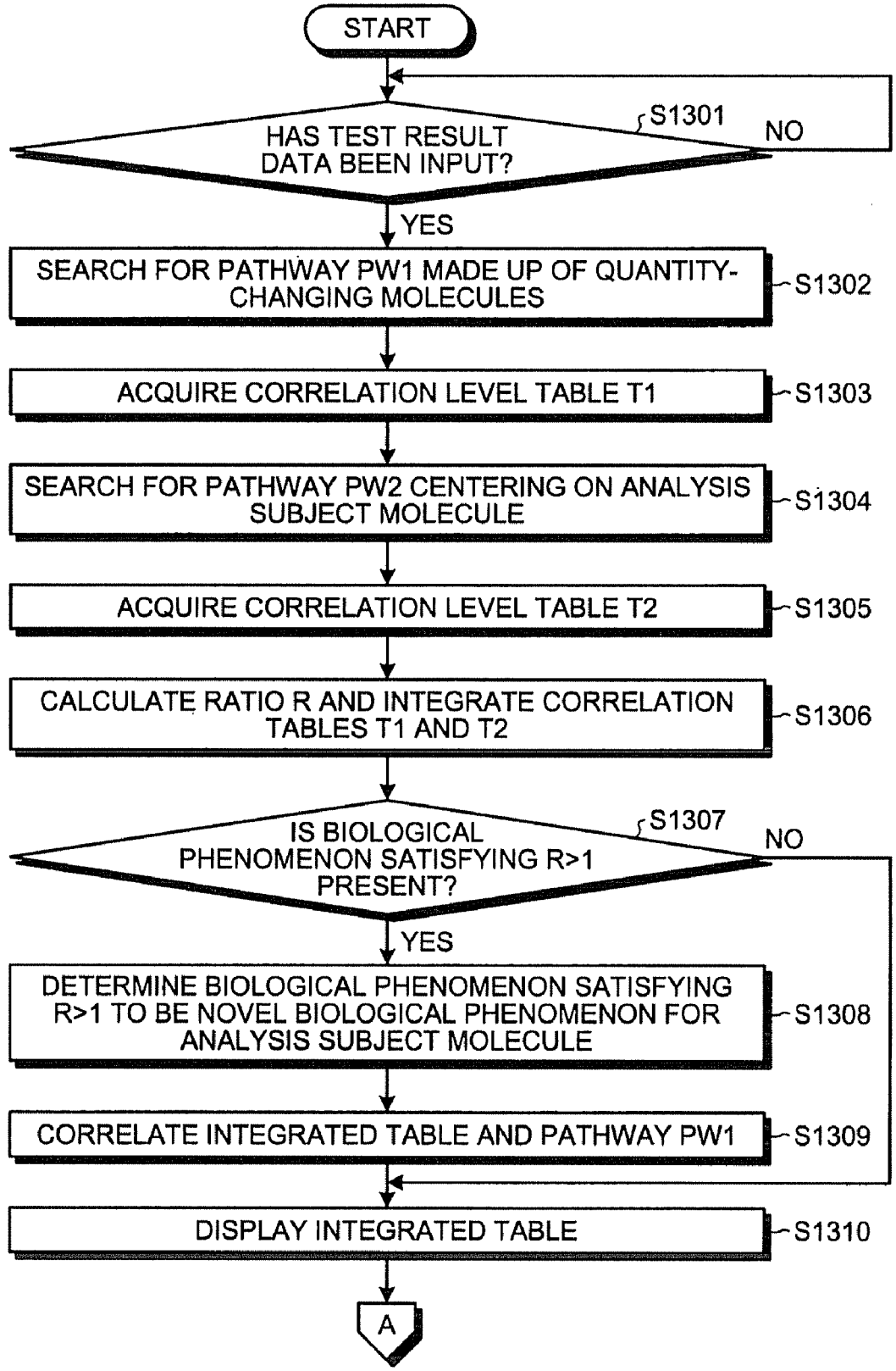
FIG. 13 is a flowchart of an analysis support procedure according to a first example.
Figure 14:
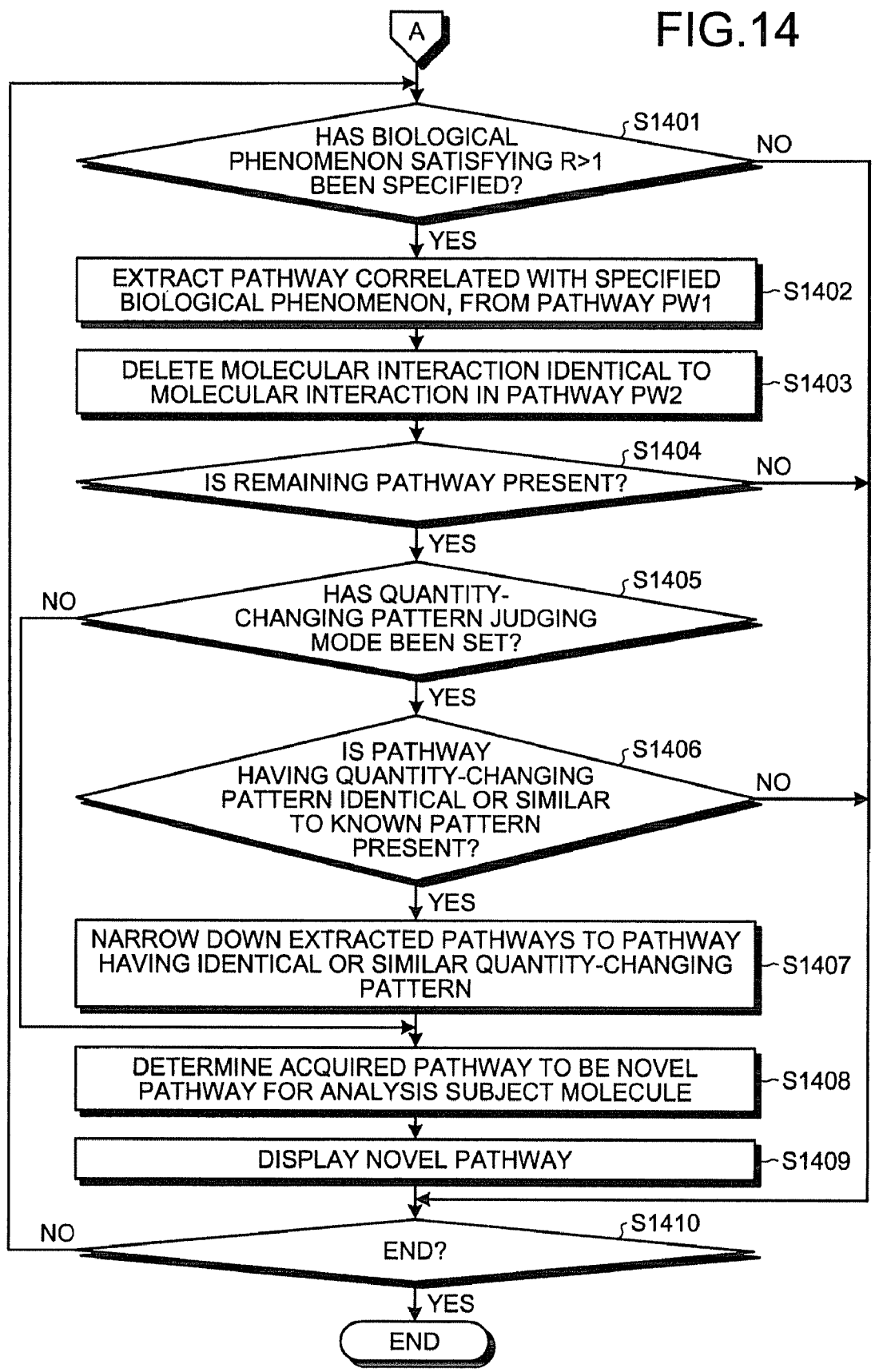
FIG. 14 is another flowchart of the analysis support procedure according to a first example.

In a first example, the analysis support apparatus 200 operates as a stand-alone apparatus. FIGS. 13 and 14 are flowcharts of an analysis support procedure according to the first example. In FIG. 13, the receiving unit 601 waits for input of the test result data 700 (step S1301: NO). When the test result data 700 is input (step S1301: YES), the first acquiring unit 602 searches for the pathway PW1 made up of quantity-changing molecules (step S1302), and acquires the correlation level table T1 indicating correlations of the quantity-changing molecules with biological phenomena (step S1303).

The second acquiring unit 603 searches for the pathway PW2 centered on an analysis subject molecule (pharmaceutical X) (step S1304), and acquires the correlation level table T2 indicating the correlation of the analysis subject molecule (pharmaceutical X) and biological phenomena (step S1305). Subsequently, a ratio R (R=α/β) is calculated, and the correlation level tables T1 and T2 are integrated (step S1306).

Whether a biological phenomenon satisfying R>1 is present is then judged (step S1307). If no biological phenomenon satisfies R>1 (step 1307: NO), the procedure proceeds to step S1310. If a biological phenomenon satisfies R>1 (step 1307:YES), the determining unit 604 determines the biological phenomenon to be a novel biological phenomenon for the analysis subject molecule (step S1308).

Subsequently, the cells 801 and 802 of the novel biological phenomena in the integrated table 800 are correlated with the pathway PW1 (step S1309). The output unit 608 then displays the integrated table 800 as depicted in FIG. 9 (step S1310).

As depicted in FIG. 14, the receiving unit 601 judges whether a biological phenomenon satisfying R>1 has been specified (step S1401). For example, the receiving unit 601 judges whether the cells 801 and 802 of the novel biological phenomena have been specified by user operation.

If a biological phenomenon satisfying R>1 has not been specified (step S1401: NO), the procedure proceeds to step S1410. If a biological phenomenon satisfying R>1 has been specified (step S1401: YES), the extracting unit 605 extracts from the pathway PW1, a pathway correlated with the specified biological phenomenon (step S1402). A molecular interaction identical to a molecular interaction in the pathway PW2 is then deleted from the extracted pathway (step S1403) to eliminate overlap between a molecular interaction included in the pathway PW2 and the extracted pathway.

Subsequently, whether a remaining pathway is present is judged (step S1404), that is, whether a pathway remains after the deletion process at step S1403, is judged (step S1404). If no pathway remains (step S1404: NO), the procedure proceeds to step S1410.

If a pathway remains (step S1404: YES), whether a quantity-changing pattern judging mode has been set is judged (step S1405). If the quantity-changing pattern judging mode has not been set (step S1405: NO), the procedure proceeds to step S1408.

If the quantity-changing pattern judging mode has been set (step S1405: YES), the judging unit 606 judges whether a pathway having a quantity-changing pattern identical to or similar to a known pattern is present (step S1406). If a pathway having an identical or similar quantity-changing pattern is not present (step S1406: NO), the procedure proceeds to step S1410.

If a pathway having an identical or similar quantity-changing pattern is present (step S1406:YES), the narrowing down unit 607 narrows down extracted pathways to the pathway having an identical or similar quantity-changing pattern (step S1407). Subsequently, the determining unit 604 determines the acquired pathway to be a novel pathway for the analysis subject molecule (step S1408).

The output unit 608 then displays the novel pathway as depicted in FIG. 10 or FIG. 11 (step S1409). Subsequently, the procedure returns to step S1401 if the procedure is not to be terminated (step S1410: NO), while the series of processes are ended if the procedure is to be ended (step S1410: YES).

The first example enables the user to build "a test system for verifying the relation between the pharmaceutical X and the molecules E, D", and develop a hypothesis on a new role of the pharmaceutical X, such as "effect on diabetes and rheumatism as obtained from the results".

A second example will be described. The second example is a server & client type analysis support system. In the second example, a server is equivalent to the analysis support apparatus 200. A client apparatus transmits necessary data to the server and receives data from the server and displays data on a display screen.

Figure 15:
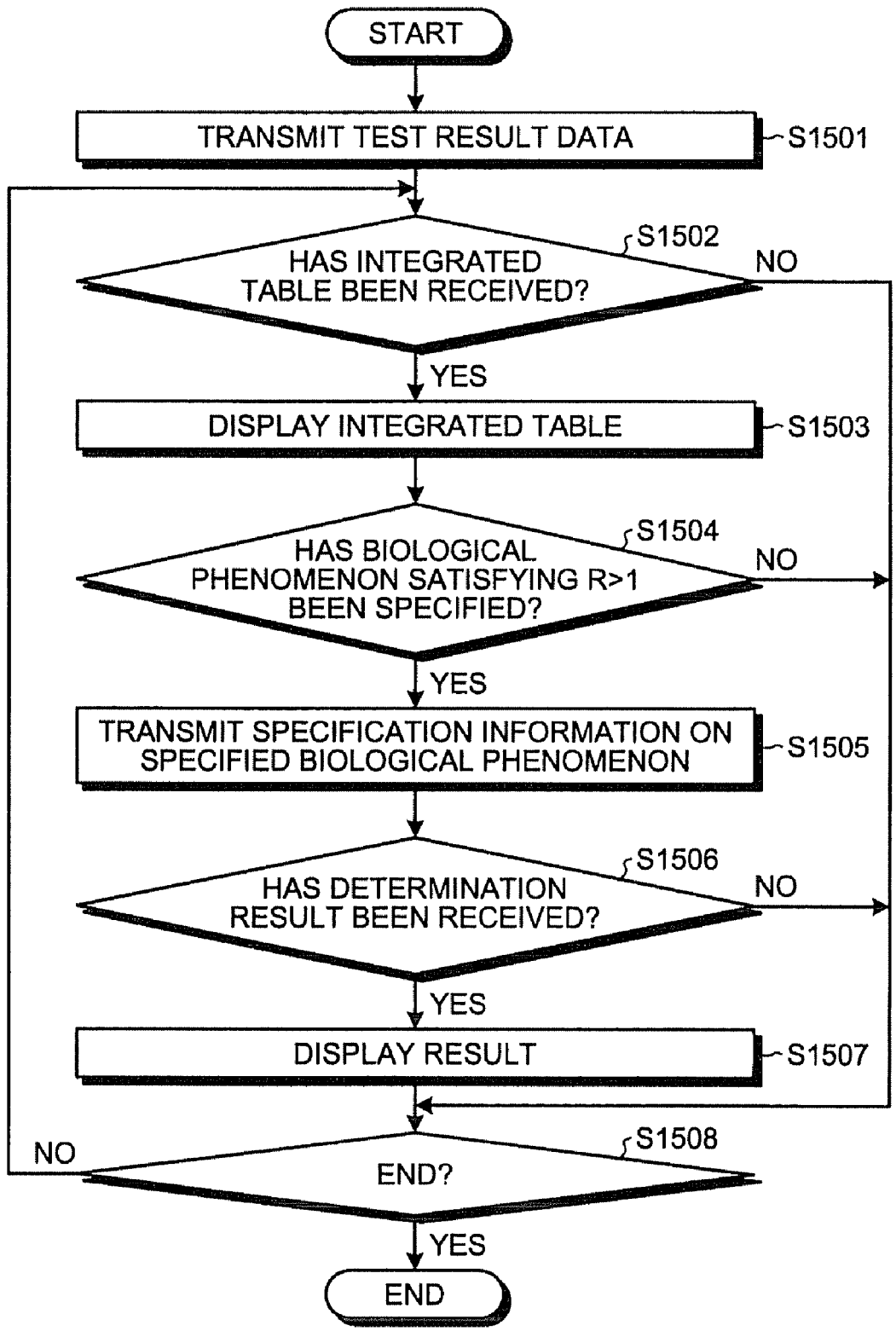
FIG. 15 is a flowchart of a procedure by a client apparatus according to a second example.

FIG. 15 is a flowchart of a procedure by the client apparatus according to the second example. First, the client apparatus transmits the test result data 700 to the server (step S1501). The client apparatus determines whether the integrated table 800 has been received from the server (step S1502). If the integrated table 800 has not been received (step S1502: NO), the procedure proceeds to step S1508.

If the integrated table 800 has been received (step S1502: YES), the integrated table 800 is displayed (step S1503). Subsequently, the client apparatus judges whether the cells 801, 802 of biological phenomena satisfying the ratio R>1 have been specified (step S1504).

If cells 801, 802 have not been specified (step S1504: NO), the procedure proceeds to step S1508. If the cells 801, 802 have been specified (step S1504: YES), specification information concerning the specified biological phenomena is transmitted (step S1505). Subsequently, whether a determination result from the server has been received is determined (step S1506).

If a determination result has not been received (step S1506: NO), the procedure proceeds to step S1508. If a determination result has been received (step S1506: YES), the determination result is displayed (step S1507). Subsequently, whether the procedure is to be terminated is determined (step S1508). If the procedure is not to be terminated (step S1508: NO), the procedure proceeds to step S1502; if the procedure is to be terminated (step S1508: YES), the series of processes by the client apparatus is terminated.

Figure 16:
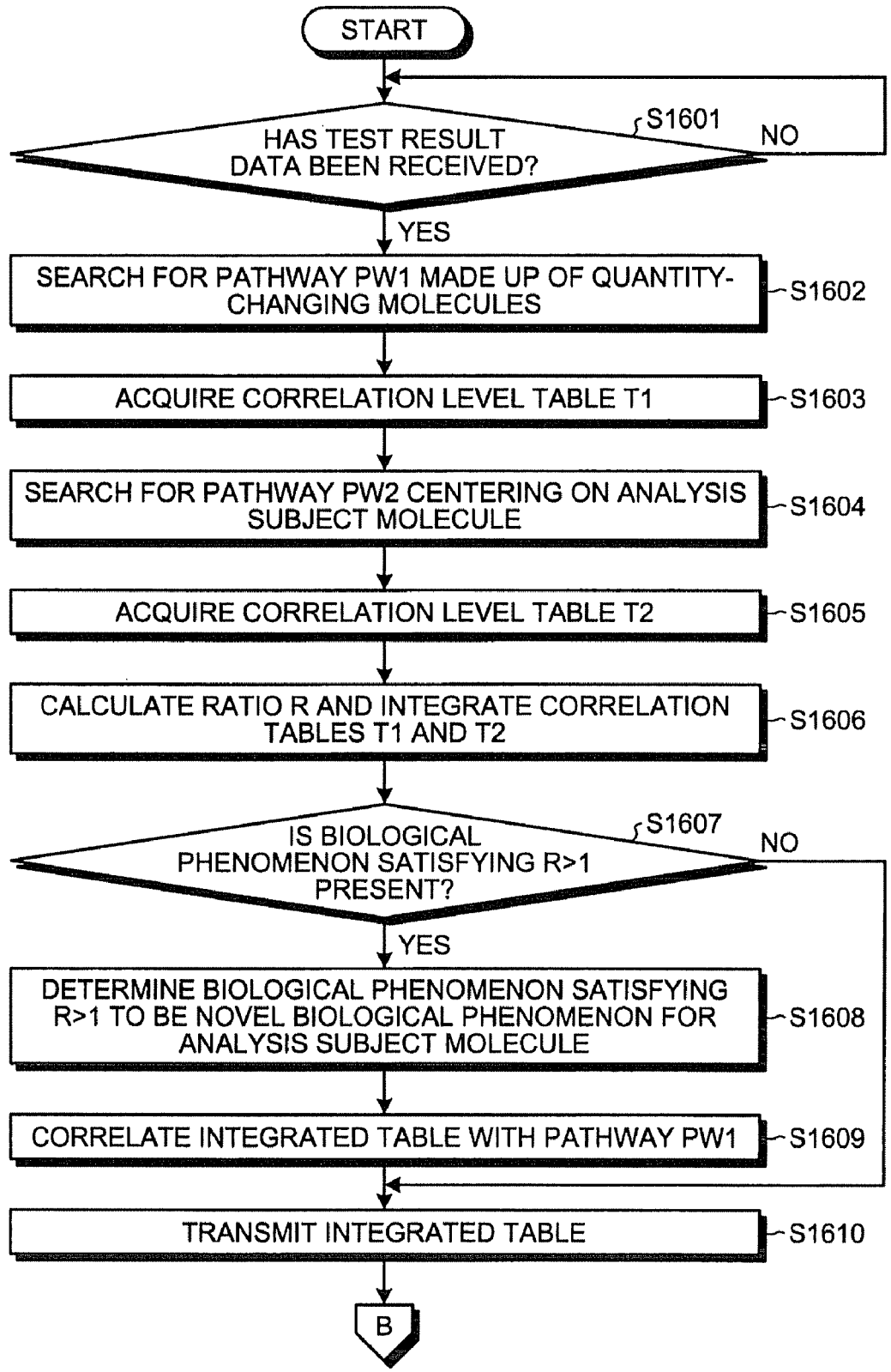
FIG. 16 is a flowchart of an analysis support procedure according to the second example.
Figure 17:
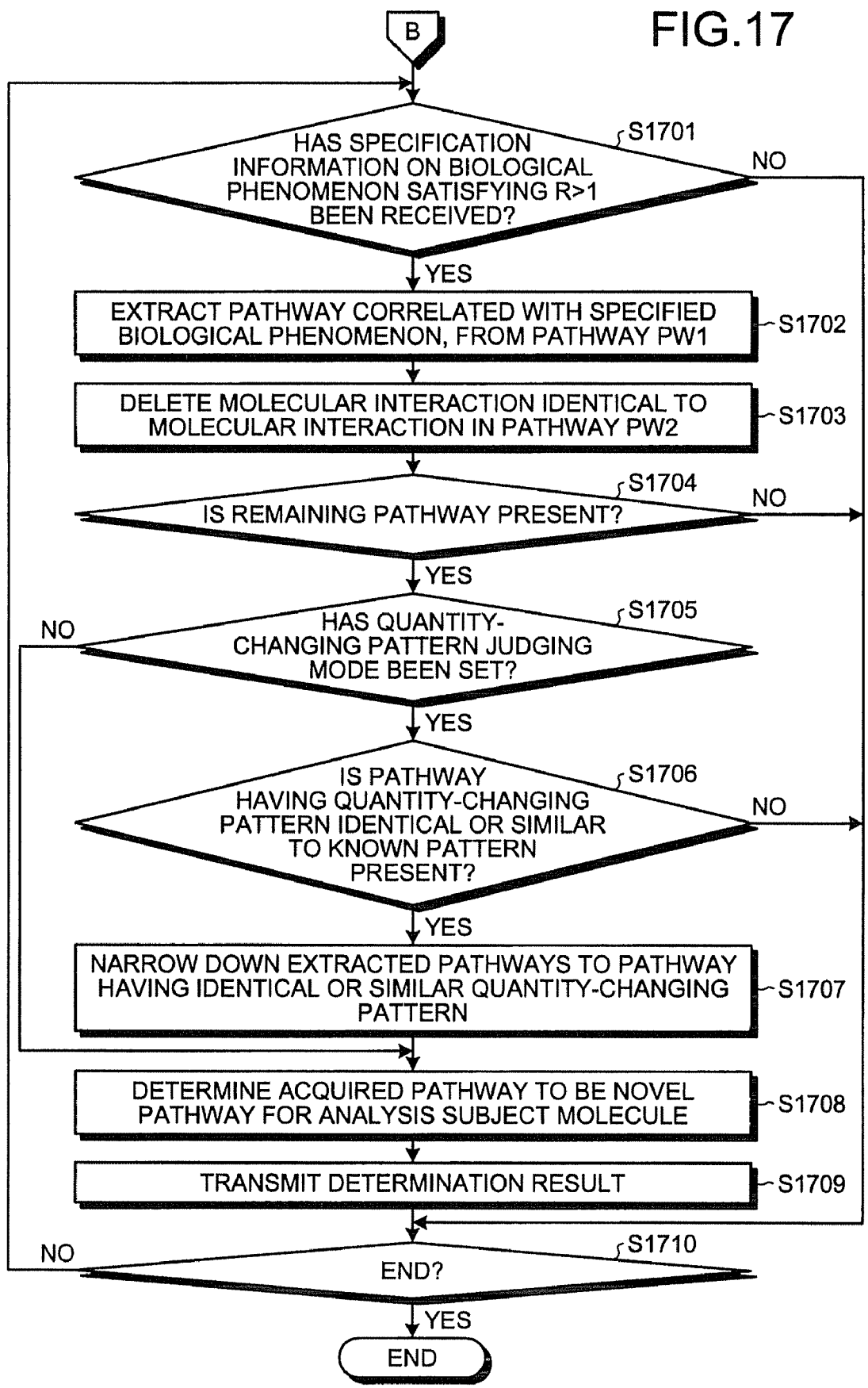
FIG. 17 is another flowchart of the analysis support procedure according to the second example.

FIGS. 16 and 17 are flowcharts of an analysis support procedure according to the second example. As depicted in FIG. 16, the receiving unit 601 waits for input of the test result data 700 (step S1601: NO). When the test result data 700 is input (step S1601: YES), the first acquiring unit 602 searches for the pathway PW1 made up of a quantity-changing molecules (step S1602), and acquires the correlation level table T1 indicating correlations of the quantity-changing molecules with biological phenomena (step S1603).

The second acquiring unit 603 searches for the pathway PW2 centered on the analysis subject molecule (pharmaceutical X) (step S1604), and acquires the correlation level table T2 indicating correlations of the analysis subject molecule (pharmaceutical X) with biological phenomena (step S1605). Subsequently, the ratio R (R=α/β) is calculated and the correlation level tables T1 and T2 are integrated (step S1606).

Whether a biological phenomenon satisfying R>1 is present is then judged (step S1607). When no biological phenomenon satisfies R>1 (step 1607: NO), the procedure proceeds to step S1610. When a biological phenomenon satisfies R>1 (step 1607: YES), the determining unit 604 determines the biological phenomenon to be a novel biological phenomenon for the analysis subject molecule (step S1608).

Subsequently, the cells 801 and 802 of the novel biological phenomena in the integrated table 800 are correlated with the pathway PW1 (step S1609). The output unit 608 then transmits the integrated table 800 to the client apparatus (step S1610). Receiving the integrated table 800, the client apparatus displays the display screen 900 of FIG. 9.

In FIG. 17, the receiving unit 601 judges whether specification information concerning a biological phenomenon satisfying R>1 has been received (step S1701). Specifically, the receiving unit 601 judges whether specification information indicating user specification of the cells 801 and 802 of the novel biological phenomena has been received from the client apparatus.

If the specification information has not been received (step S1701: NO), the procedure proceeds to step S1710. If the specification information has been received (step S1701: YES), the extracting unit 605 extracts a pathway correlated with the specified biological phenomenon from the pathway PW1 (step S1702). A molecular interaction identical to a molecular interaction in the pathway PW2 is then deleted from the extracted pathway (step S1703), thereby preventing overlap between a molecular interaction included in the pathway PW2 and the extracted pathway.

Subsequently, whether a remaining pathway is present is judged (step S1704), that is, whether a pathway remains after the deletion process at step S1703, is judged (step S1704). If no pathway remains (step S1704: NO), the procedure proceeds to step S1710.

If a pathway remains (step S1704: YES), whether the quantity-changing pattern judging mode has been set is determined (step S1705). If the quantity-changing pattern judging mode has not been set (step S1705: NO), the procedure proceeds to step S1708.

If the quantity-changing pattern judging mode has been set (step S1705: YES), the judging unit 606 judges whether a pathway having a quantity-changing pattern identical or similar to a known pattern is present (step S1706). If a pathway having an identical or similar quantity-changing pattern is not present (step S1706: NO), the procedure proceeds to step S1710.

If a pathway having an identical or similar quantity-changing pattern is present (step S1706: YES), the narrowing down unit 607 narrows down extracted pathways to the pathway having an identical or similar quantity-changing pattern (step S1707). Subsequently, the determining unit 604 determines the acquired pathway to be a novel pathway for the analysis subject molecule (step S1708).

The output unit 608 then transmits the novel pathway to the client apparatus (step S1709). Receiving this determination result, the client apparatus displays the novel pathway as depicted in FIG. 10 or FIG. 11. Subsequently, the procedure returns to step S1701 if the procedure is not to be terminated (step S1710: NO), while the series of processes by the server is terminated if the procedure is to be terminated (step S1710: YES).

Similar to the first example, the second example also enables the user to build "a test system for verifying the relation between the pharmaceutical X and the molecules E, D" and set up a hypothesis on a new role of the pharmaceutical X, such as "effect on diabetes and rheumatism as obtained from the results".

A third example will be described. The third example is a server & client type analysis support system, similar to the second example. In the third example, therefore, a server is equivalent to the analysis support apparatus 200. A client apparatus transmits necessary data to the server and receives data from the server to display the data on a display screen. In the third example, the server collects the test result data 700 in advance from the client apparatus. Upon receiving a request for analysis of the analysis subject molecule X from a given client apparatus, the server executes an analysis support process.

Figure 18:
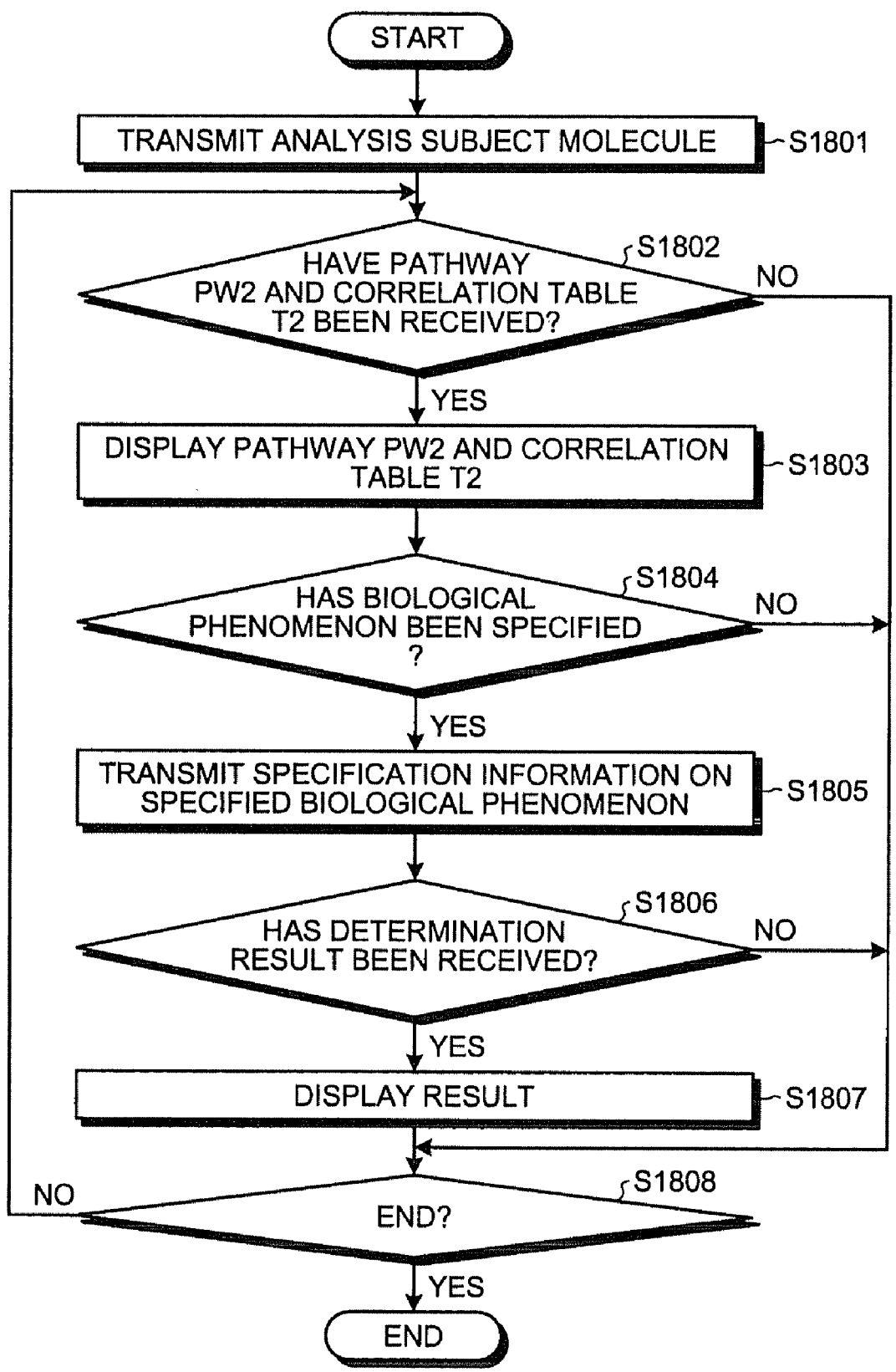
FIG. 18 is a flowchart of a procedure by the client apparatus according to a third example.

FIG. 18 is a flowchart of a procedure by the client apparatus according to the third example. First, the client apparatus specifies an analysis subject molecule and transmits the analysis subject molecule together with an analysis request to the server (step S1801). The client apparatus then judges whether the pathway PW2 and the correlation level table T2 have been received from the server (step S1802). If the pathway PW2 and table T2 have not been received (step S1802: NO), the procedure proceeds to step S1808.

If the pathway PW2 and table T2 have been received (step S1802: YES), the received pathway PW2 and correlation level table T2 are displayed (step S1803). Subsequently, the client apparatus judges whether a cell of an arbitrary biological phenomenon in the correlation level table T2 has been designated (step S1804).

If a biological phenomenon has not been designated (step S1804: NO), the procedure proceeds to step S1808. If a biological phenomenon has been designated (step S1804: YES), specification information concerning the specified biological phenomenon is transmitted (step S1805). Subsequently, whether a determination result from the server has been received is determined (step S1806).

If a determination result has not been received (step S1806: NO), the procedure proceeds to step S1808. If a determination result has been received (step S1806: YES), the determination result is displayed (step S1807). Subsequently, whether the procedure is to be terminated is determined (step S1808). If the procedure is not to be terminated (step S1808: NO), the procedure proceeds to step S1802; if the procedure is to be terminated (step S1808: YES), the series of processes by the client apparatus is terminated.

Figure 19:
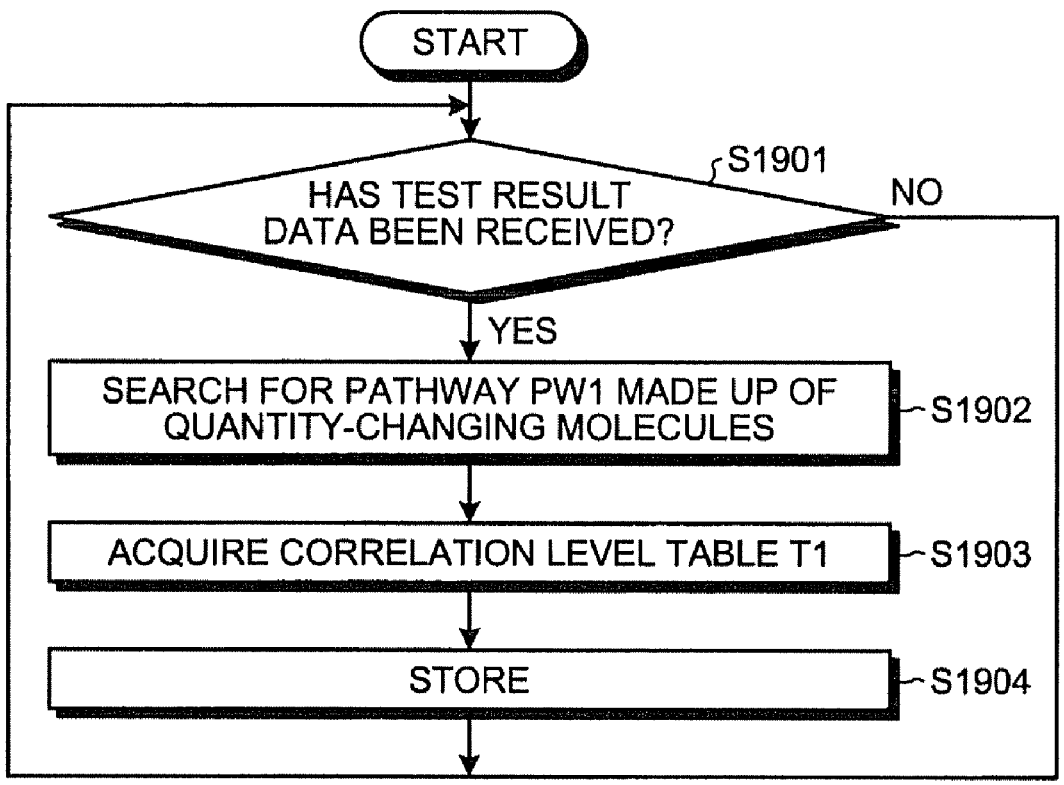
FIG. 19 is a flowchart of a regular procedure by a server.

A regular procedure by the server will be described. FIG. 19 is a flowchart of the regular procedure by the server. As depicted in FIG. 19, the receiving unit 601 waits for input of the test result data 700 (step S1901: NO). When the test result data 700 is input (step S1901: YES), the first acquiring unit 602 searches for the pathway PW1 made up of quantity-changing molecules (step S1902), and acquires the correlation level table T1 indicating correlations of the quantity-changing molecules with biological phenomena (step S1903). The acquired pathway PW1 and correlation level table T1 are stored together with the test result data 700 in the server (step S1904), after which the procedure returns to step S1901.

In this manner, the server is capable of constantly collecting the test result data 700 and keeping the pathway PW1 and the correlation level table T1. The server is thus capable of accumulating information concerning various effects, such as the effect of administration of the pharmaceutical X and the effect of deficiency of the gene X, thereby facilitating improvement in the retrieval rate of a new role of an analysis subject molecule.

Figure 20:
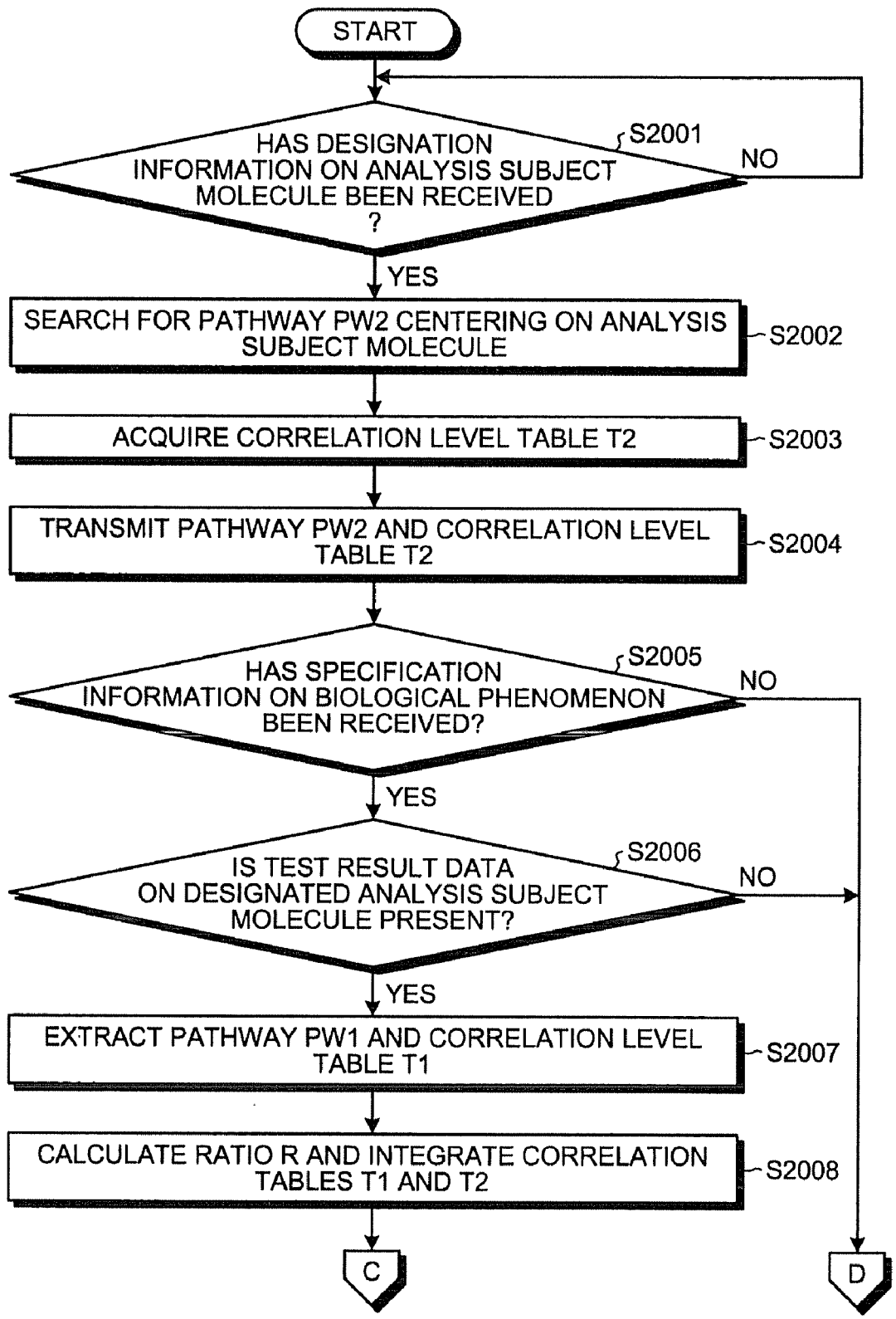
FIG. 20 is a flowchart of an analysis support procedure by the server.

FIG. 20 is a flowchart of (the first half of) an analysis support procedure by the server. As depicted in FIG. 20, the receiving unit 601 waits for reception of designation information designating an analysis subject molecule (step S2001: NO). When the designation information is received (step S2001: YES), the second acquiring unit 603 searches for the pathway PW2 centered on the analysis subject molecule (pharmaceutical X) (step S2002), and acquires the correlation level table T2 indicating correlations between the analysis subject molecule (pharmaceutical X) and biological phenomena (step S2003).

The server then transmits the pathway PW2 and the correlation level table T2 to the client apparatus that has transmitted the specification information (step S2004). Subsequently, the server judges whether specification information specifying a biological phenomenon has been received from the client apparatus (step S2005).

If specification information has not been received (step S2005: NO), the procedure proceeds to step S2109 of FIG. 21. If specification information has been received (step S2005: YES), the server judges whether test result data 700 for the analysis subject molecule designated by the designation information received at step S2001 is present among the test result data 700 stored at step S1904 (step S2006).

If such test result data 700 is not present (step S2006: NO), the procedure proceeds to step S2109 of FIG. 21. If such test result data 700 is present (step S2006: YES), the pathway PW1 and correlation level table T1 stored together with the test result data 700 at step S1904 are extracted (step S2007). Subsequently, the ratio R (R=α/β) is calculated and the correlation level tables T1 and T2 are integrated (step S2008), and the procedure proceeds to step S2101.

FIG. 21 is a flowchart of (the second half of) the analysis support procedure by the server. In FIG. 21, the server judges whether the specified biological phenomenon received as the specification information at step S2005 satisfies R>1 (step S2101). If the biological phenomenon does not satisfy R>1 (step S2101: NO), the biological phenomenon has no new role. The procedure thus proceeds to step S2109, at which a result is transmitted indicating that the specified biological phenomenon is not novel. If the biological phenomenon satisfies R>1 (step S2101: YES), the extracting unit 605 extracts from the pathway PW1, a pathway correlated with the biological phenomenon (step S2102). A molecular interaction identical to a molecular interaction in the pathway PW2 is then deleted from the extracted pathway (step S2103), thereby preventing overlap between a molecular interaction included in the pathway PW2 and the extracted pathway.

Subsequently, whether a remaining pathway is present is judged (step S2104), that is, whether a pathway remains after the deletion process at step S2103, is judged (step S2104). If no pathway remains (step S2104: NO), the procedure proceeds to step S2109, at which a result is transmitted indicating that the specified biological phenomenon is not novel.

If a pathway remains (step S2104: YES), whether the quantity-changing pattern judging mode has been set is determined (step S2105). If the quantity-changing pattern judging mode has not been set (step S2105: NO), the procedure proceeds to step S2108.

If the quantity-changing pattern judging mode has been set (step S2105: YES), the judging unit 606 judges whether a pathway having a quantity-changing pattern identical or similar to a known pattern is present (step S2106). If a pathway having an identical or similar quantity-changing pattern is not present (step S2106: NO), the procedure proceeds to step S2109, at which a result is transmitted indicating that the occurrence of the specified biological phenomenon is uncertain.

If a pathway having an identical or similar quantity-changing pattern is present (step S2106: YES), the narrowing down unit 607 narrows down extracted pathways to the pathway having an identical or similar quantity-changing pattern (step S2107). Subsequently, the determining unit 604 determines the acquired pathway to be a novel pathway for the analysis subject molecule (step S2108).

The output unit 608 then transmits the integrated table 800 and the novel pathway to the client apparatus (step S2109). Receiving this determination result, the client apparatus displays the integrated table 800 and the novel pathway as depicted in FIG. 10 or FIG. 11. The screen of FIG. 10 is displayed when the user specifies "diabetes" as an arbitrary biological phenomenon at step S1804, while the screen of FIG. 11 is displayed when the user specifies "rheumatism". Subsequently, the procedure returns to step S2101 if the procedure is not to be terminated (step S2110: NO), while the series of processes by the server is terminated if the procedure is to be terminated (step S2110: YES).

According to the third example, even if the user does not know which biological phenomenon is highly novel among biological phenomena presented in the correlation level table T2, the user is able to build "a test system for verifying the relation between the pharmaceutical X and the molecules E, D" and set up a hypothesis on a new role of the pharmaceutical X, such as "effect on diabetes and rheumatism as obtained from the results".

In this manner, according to the above embodiment (including the first to third examples), the known information 102 concerning the analysis subject molecule X is classified, and the test result analysis information 101 showing that the molecules D, E, and F have been affected by the analysis subject molecule X in a test, is classified. The classified test result analysis information 101 and known information 102 are compared as depicted in FIGS. 9 to 11, effecting the discovery of a new role of the analysis subject molecule X.

Comparison of the known information 102 and the test result analysis information 101 acquired from a test result means that "the relation between the analysis subject molecule X and a biological phenomenon is observed through a test". In other words, in the study of the analysis subject molecule X, not only is the known information 102 analyzed, but the significance of a conducted test is increased. Hence, carrying out such comparison enhances the value of a test result (test result analysis information 101) as an asset.

To discover a new role related to the analysis subject molecule X from a pathway in a conventional manner, one must read many papers describing molecules and molecular interactions making up the pathway. According to the present embodiment, information such as "diseases for which correlation with the pharmaceutical X is novel include diabetes and rheumatism" is presented in a manner as depicted in FIG. 9, thereby limiting the papers to be read to the fields of "diabetes" and "rheumatism".

As depicted in FIGS. 10 and 11, interactions that are between quantity-changing molecules and correlated with such biological phenomena (diseases) are also presented, thereby narrowing down the papers to be read, from papers concerning biological phenomena (diseases) to a smaller range, molecules. In the present embodiment, therefore, the number of papers to be read upon pathway analysis is reduced, which contributes to a reduction in the burden on a researcher (user) and in the period for the development of a new pharmaceutical.

A researcher must read many papers to discover, from a pathway, a new role related to the analysis subject molecule X. Usually, the researcher makes a judgment on which paper to read in such a case. In the present embodiment, the known information 102 concerning the analysis subject molecule X is compared with a test result (test result analysis information 101), as depicted in FIG. 9, thereby limiting the range of papers to be read, based on numerical value, and thus enabling analysis of the novelty of a molecule from which the subjectivity and biased experiences of the researcher are excluded.

As described above, the present embodiment enables a new role of the analysis subject molecule X to be sought. Developing and adding new applicable diseases and dosage forms to pharmaceuticals already on the market is called application expansion. This is very effective as a measure against generic drugs. Particularly, expansion of applicable diseases leads to an extension of the term of patent rights on pharmaceutical usage, thus essential as a patent license strategy. For example, if a new role of a pharmaceutical initially marketed as a cold medication is discovered to be effective against headaches, the term of patent right on the pharmaceutical can be extended to maintain profits. In this manner, when the analysis subject molecule X is a pharmaceutical, diseases to which the pharmaceutical is applicable are expanded to extend the term of patent rights on the pharmaceutical, which enables the maintenance and expansion of profits for a pharmaceutical company and an academic organization possessing the patent rights.

When the analysis subject molecule X is a gene, the gene is deficient, and a pathway is built from molecules affected by the deficient gene to search for a new role of the deficient gene, thereby leading to discovery of a correlation between the gene and a disease that has not been reported thus far with respect to the gene. This is very beneficial in terms of medical/clinical research. Enhancing the value of test data (test result analysis information 101) as an asset is beneficial regardless of whether the test data belongs to a private business or a public academic society.

The analysis support method described in the present embodiment may be implemented by executing a prepared program on a computer such as a personal computer and a workstation. The program is stored on a computer-readable recording medium such as a hard disk, a flexible disk, a CD-ROM, an MO, and a DVD, read out from the recording medium, and executed by the computer. The program may be a transmission medium that can be distributed through a network such as the Internet.

As described above, analysis support apparatus, an analysis support method, and an analysis support program are useful for analyzing a pathway indicating molecular interactions with a molecule, such as protein, compound, gene, and pharmaceutical.

According to the analysis support program, the analysis support apparatus, and the analysis support method, a novel biological phenomenon (disease, side effect, etc.) correlated with the analysis subject molecule can be discovered by comparing the second pathway indicating molecular interactions with the analysis subject molecule and the first pathway acquired from a test result that does not include the analysis subject molecule. "Novel biological phenomenon" means a biological phenomenon that cannot be acquired from the second pathway (novel biological phenomenon) and also means a biological phenomenon that can be acquired from the second pathway but is downplayed in the second pathway (novel biological phenomenon).

According to the analysis support program, the analysis support apparatus, and the analysis support method, a biological phenomenon that is evaluated to be low in the second pathway while evaluated to be high in the first pathway can be discovered.

According to the analysis support program, the analysis support apparatus, and the analysis support method, the subject of study can be narrowed down, ranging from biological phenomena (diseases) to molecules.

According to the analysis support program, the analysis support apparatus, and the analysis support method, a novel and probable pathway can be identified.

The analysis support program, the analysis support apparatus, and the analysis support method effect searches for a new role of a molecule, thereby contributing to a reduction in the burden on a user, the promotion of new pharmaceutical research/development, and an extension of the term of patent right.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A non-transitory computer-readable recording medium storing therein an analysis support program when executed causing a computer to execute a process comprising:
   receiving test result data identifying a molecule administered to a test subject or a deficient molecule, as an analysis subject molecule, and quantity-changing molecules that have changed in quantity due to administration or deficiency of the analysis subject molecule in the test subject;
   acquiring a first pathway indicating an interaction between the quantity-changing molecules identified by the test result data;
   acquiring a second pathway indicating a molecular interaction with the analysis subject molecule, from a database storing therein for each molecular interaction, a type;
   determining from among biological phenomena correlated with the interaction between quantity-changing molecules of the first pathway, a biological phenomenon other than a biological phenomenon correlated with a molecular interaction of the second pathway to be a novel biological phenomenon caused by administration or deficiency of the analysis subject molecule; and
   outputting a determination result obtained at the determining.

2. The computer recording medium according to claim 1, wherein
   the outputting includes outputting the determination result on a display screen.

3. The non-transitory computer-readable recording medium according to claim 1, wherein
   the outputting includes transmitting the determination result to a requester requesting the determination result.

4. The non-transitory computer-readable recording medium according to claim 1, wherein
   the acquiring of the first pathway includes acquiring a first correlation level representing correlation strength of a biological phenomenon correlated with the interaction between quantity-changing molecules of the first pathway,
   the acquiring of the second pathway includes acquiring a second correlation level representing correlation strength of a biological phenomenon correlated with the molecular interaction of the second pathway, and
   the determining includes, by a comparison of the first correlation level and the second correlation level for a given biological phenomenon, determining the given biological phenomenon to be the novel biological phenomenon.

5. The non-transitory computer-readable recording medium according to claim 4, wherein
   the determining includes determining a biological phenomenon for which the first correlation level is greater than the second correlation level to be the novel biological phenomenon.

6. The non-transitory computer-readable recording medium according to claim 1 and storing therein the analysis support program causing the computer to execute the process further comprising extracting, from the first pathway, a pathway indicating a molecular interaction correlated with the novel biological phenomenon determined at the determining, wherein
the determining includes determining the extracted pathway to be a novel pathway caused by administration or deficiency of the analysis subject molecule.

7. The non-transitory computer-readable recording medium according to claim 6, wherein
the test result data further includes information identifying a change in quantity of each of the quantity-changing molecules,
the analysis support program causes the computer to execute the process further comprising:
judging whether the quantity-changing molecules have a quantity-changing pattern identical to or similar to a known quantity-changing pattern, based on the information identifying a change in the quantity of each of the quantity-changing molecules; and
narrowing down, based on a judgment result obtained at the judging, pathways extracted at the extracting, wherein
the determining includes determining a pathway resulting from narrowing down at the narrowing down to be a novel pathway caused by administration or deficiency of the analysis subject molecule.

8. The non-transitory computer-readable recording medium according to claim 6, wherein
the receiving includes receiving specification of a novel biological phenomenon, and
the outputting includes displaying the novel pathway on the display screen if specification of the novel biological phenomenon is received at the receiving.

9. The non-transitory computer-readable recording medium according to claim 6, wherein
the receiving includes receiving specification of the novel biological phenomenon from a requester requesting the determination result, and
the outputting includes transmitting the novel pathway to the requester if specification of the novel biological phenomenon from the requester is received at the receiving.

10. A non-transitory computer-readable recording medium storing therein an analysis support program when executed causing a computer to execute a process comprising:
receiving test result data identifying a molecule administered to a test subject or a deficient molecule, as an analysis subject molecule, and quantity-changing molecules that have changed in quantity due to administration or deficiency of the analysis subject molecule in the test subject;
acquiring a first pathway indicating an interaction between the quantity-changing molecules identified by the test result data;
acquiring a second pathway indicating a molecular interaction with the analysis subject molecule, from a database storing therein for each molecular interaction, a type;
extracting from the first pathway, a pathway indicating an interaction that is between quantity-changing molecules and correlated with a biological phenomenon other than a biological phenomenon correlated with the molecular interaction of the second pathway;
determining the extracted pathway to be a novel pathway caused by administration or deficiency of the analysis subject molecule; and
outputting a determination result obtained at the determining.

11. The non-transitory computer-readable recording medium according to claim 10, wherein
the test result data further includes information identifying a change in quantity of each of the quantity-changing molecules,
the analysis support program causes the computer to execute the process further comprising:
judging whether the quantity-changing molecules have a quantity-changing pattern identical to or similar to a known quantity-changing pattern, based on the information identifying a change in the quantity of each of the quantity-changing molecules; and
narrowing down, based on a judgment result obtained at the judging, pathways extracted at the extracting, wherein
the determining includes determining a pathway resulting from narrowing down at the narrowing down to be a novel pathway caused by administration or deficiency of the analysis subject molecule.

12. The non-transitory computer-readable recording medium according to claim 10, wherein
the receiving includes receiving specification of a novel biological phenomenon, and
the outputting includes displaying the novel pathway on the display screen if specification of the novel biological phenomenon is received at the receiving.

13. The non-transitory computer-readable recording medium according to claim 10, wherein
the receiving includes receiving specification of the novel biological phenomenon from a requester requesting the determination result, and
the outputting includes transmitting the novel pathway to the requester if specification of the novel biological phenomenon from the requester is received at the receiving.

14. An analysis support apparatus comprising:
a receiving unit that receives test result data identifying a molecule administered to a test subject or a deficient molecule, as an analysis subject molecule, and quantity-changing molecules that have changed in quantity due to administration or deficiency of the analysis subject molecule in the test subject;
a first acquiring unit that acquires a first pathway indicating an interaction between the quantity-changing molecules identified by the test result data;
a second acquiring unit that acquires a second pathway indicating a molecular interaction with the analysis subject molecule, from a database storing therein for each molecular interaction, a type;
a determining unit that from among biological phenomena correlated with the interaction between quantity-changing molecules of the first pathway, determines a biological phenomenon other than a biological phenomenon correlated with a molecular interaction of the second pathway to be a novel biological phenomenon caused by administration or deficiency of the analysis subject molecule; and
an output unit that outputs a determination result obtained by the determining unit.

15. An analysis support apparatus comprising:
a receiving unit that receives test result data identifying a molecule administered to a test subject or a deficient molecule, as an analysis subject molecule, and quantity-changing molecules that have changed in quantity due to administration or deficiency of the analysis subject molecule in the test subject;
a first acquiring unit that acquires a first pathway indicating an interaction between the quantity-changing molecules identified by the test result data;
a second acquiring unit that acquires a second pathway indicating a molecular interaction with the analysis subject molecule, from a database storing therein for each molecular interaction, a type;

an extracting unit that extracts from the first pathway, a pathway indicating an interaction that is between quantity-changing molecules and correlated with a biological phenomenon other than a biological phenomenon correlated with the molecular interaction of the second pathway;

a determining unit that determines the extracted pathway to be a novel pathway caused by administration or deficiency of the analysis subject molecule; and an output unit that outputs a determination result obtained by the determining unit.

16. An analysis support method comprising:

receiving test result data identifying a molecule administered to a test subject or a deficient molecule, as an analysis subject molecule, and quantity-changing molecules that have changed in quantity due to administration or deficiency of the analysis subject molecule in the test subject;

acquiring a first pathway indicating an interaction between the quantity-changing molecules identified by the test result data;

acquiring a second pathway indicating a molecular interaction with the analysis subject molecule, from a database storing therein for each molecular interaction, a type;

determining from among biological phenomena correlated with the interaction between quantity-changing molecules of the first pathway, a biological phenomenon other than a biological phenomenon correlated with a molecular interaction of the second pathway to be a novel biological phenomenon caused by administration or deficiency of the analysis subject molecule; and outputting a determination result obtained at the determining.

17. An analysis support method comprising:

receiving test result data identifying a molecule administered to a test subject or a deficient molecule, as an analysis subject molecule, and quantity-changing molecules that have changed in quantity due to administration or deficiency of the analysis subject molecule in the test subject;

acquiring a first pathway indicating an interaction between the quantity-changing molecules identified by the test result data;

acquiring a second pathway indicating a molecular interaction with the analysis subject molecule, from a database storing therein for each molecular interaction, a type;

extracting from the first pathway, a pathway indicating an interaction that is between quantity-changing molecules and correlated with a biological phenomenon other than a biological phenomenon correlated with the molecular interaction of the second pathway;

determining the extracted pathway to be a novel pathway caused by administration or deficiency of the analysis subject molecule; and outputting a determination result obtained at the determining.

* * * * *